(12) United States Patent
Cardozo et al.

(10) Patent No.: US 7,638,319 B2
(45) Date of Patent: Dec. 29, 2009

(54) METHOD FOR DETERMINING CO-RECEPTOR SELECTIVITY OF HUMAN IMMUNODEFICIENCY VIRUS-1

(75) Inventors: Timothy Cardozo, New York, NY (US); Susan Zolla-Pazner, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/369,010

(22) Filed: Mar. 7, 2006

(65) Prior Publication Data

US 2007/0072200 A1 Mar. 29, 2007

Related U.S. Application Data

(60) Provisional application No. 60/658,574, filed on Mar. 7, 2005.

(51) Int. Cl.
*C12N 7/00* (2006.01)
*C12Q 1/00* (2006.01)

(52) U.S. Cl. .................................. 435/235.1; 435/4

(58) Field of Classification Search ............... None
See application file for complete search history.

(56) References Cited

OTHER PUBLICATIONS

Fa-xin et al., Biological characteristics of HIV-1 isolates circulating in China are linked to its env V3 loop sequence variability, Zhonghua yi xue za zhi ( China ), Dec 2, 2004, 84 (23):1968-72 (Abstract only).*

Resch et al., Improved success of phenotype prediction of the human immunodeficiency vrus type I from envelope variable loop 3 sequence using neural networks, Virology, 2001, 288:51-62.*

Xiao et al., CCR5 coreceptor usage of non-syncytium-inducing primary HIV-1 is independent of phylogenetically distinct global HIV-1 isolates: delination of consensus motif in the V3 domain that predicts CCR-5 usage, Virology, 1998, 240:83-92.*

* cited by examiner

*Primary Examiner*—Gary B Nickol
*Assistant Examiner*—Nicole Kinsey White
(74) *Attorney, Agent, or Firm*—Browdy & Neimark, PLLC

(57) ABSTRACT

Newly discovered structural characteristic of the gp120 V3 loop have resulted in a "rule" or algorithm, that is used in a method for determining whether a subject is infected with HIV-1 virus that expresses selectivity for CXCR4 or CCR5 chemokine receptors. A positively charged surface patch defined by V3 loop residues 11 and 24 or 25 at the base of the β-strands in the V3 loop and the homologous β2-β3 chemokine hairpin is responsible for CXCR4 receptor selection. Thus a method for detecting the presence of HIV-1 virus that is selective for X4-co-receptors in a subject infected with HIV-1 or suspected of being infected, from the amino acid sequence of at least a part of the HIV-1 gp120 V3 region peptide that includes residues 11, 24 and 25, or from the nucleotide sequence of a nucleic acid encoding said V3 region peptide, is disclosed.

14 Claims, 3 Drawing Sheets

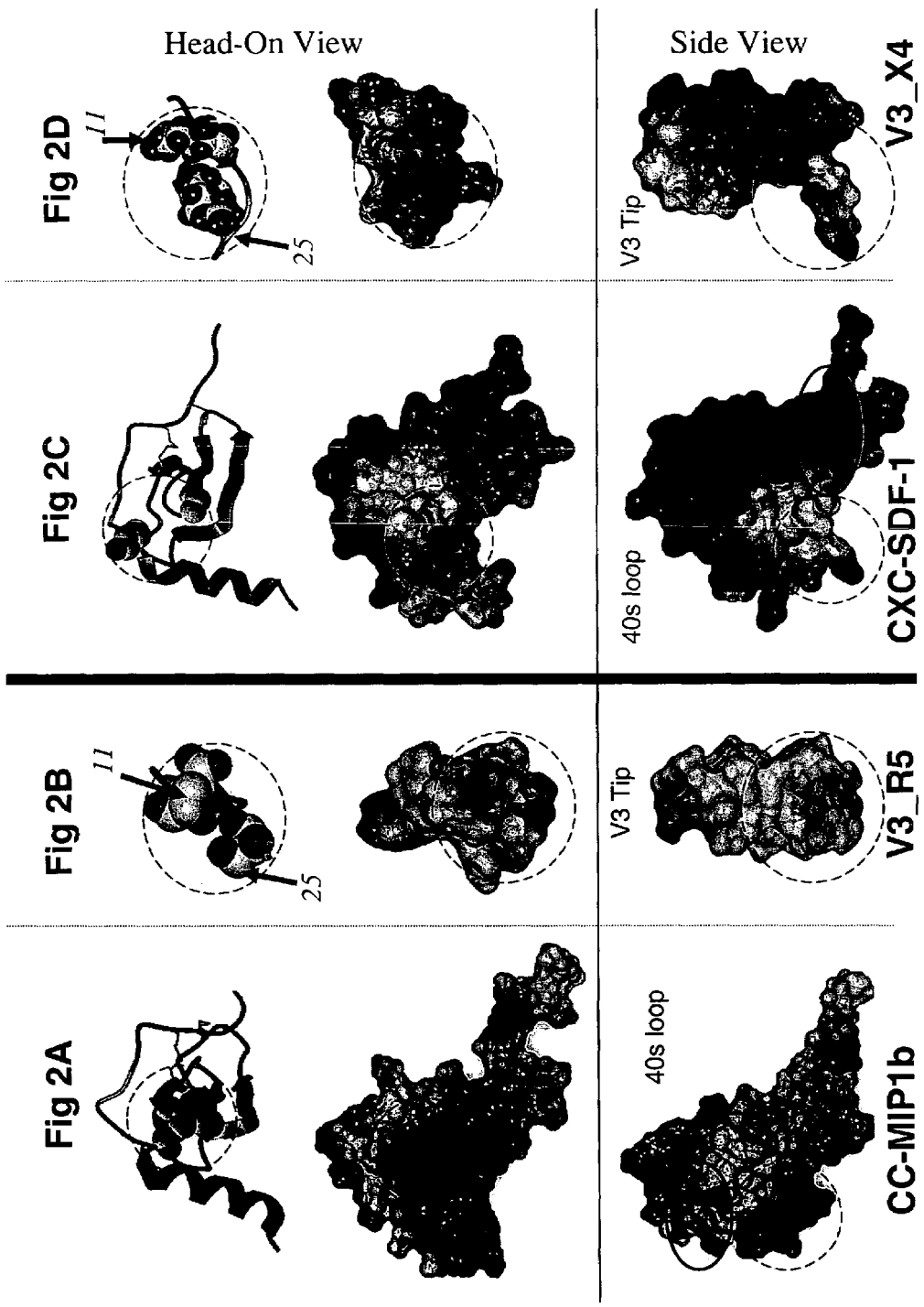

SEQUENCE LISTING

```
<160> NUMBER OF SEQ ID NOS: 82

<210> SEQ ID NO 1
<211> LENGTH: 35
<212> TYPE: PRT
<213> ORGANISM: Human immunodeficiency virus type-1

<400> SEQUENCE: 1

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

<210> SEQ ID NO 2
<211> LENGTH: 35
<212> TYPE: PRT
<213> ORGANISM: Human immunodeficiency virus type-1

<400> SEQUENCE: 2

Cys Thr Arg Pro Ser Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
```

```
                    20                  25                  30

Ala His Cys
        35

<210> SEQ ID NO 3
<211> LENGTH: 35
<212> TYPE: PRT
<213> ORGANISM: Human immunodeficiency virus type-1

<400> SEQUENCE: 3

Cys Thr Arg Pro Asn Asn Asn Thr Arg Lys Ser Ile Thr Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 4
<211> LENGTH: 14
<212> TYPE: PRT
<213> ORGANISM: Human immunodeficiency virus type-1

<400> SEQUENCE: 4

Lys Arg Ile His Ile Gly Pro Gly Arg Ala Phe Tyr Thr Thr
1               5                   10

<210> SEQ ID NO 5
<211> LENGTH: 17
<212> TYPE: PRT
<213> ORGANISM: Human immunodeficiency virus type-1

<400> SEQUENCE: 5

Arg Lys Ser Ile Arg Ile Gln Arg Gly Pro Gly Arg Ala Phe Val Thr
1               5                   10                  15

Ile

<210> SEQ ID NO 6
<211> LENGTH: 62
<212> TYPE: PRT
<213> ORGANISM: Homo sapiens

<400> SEQUENCE: 6

Ser Tyr Arg Cys Pro Cys Arg Phe Phe Glu Ser His Val Ala Arg Ala
1               5                   10                  15

Asn Val Lys His Leu Lys Ile Leu Asn Thr Pro Asn Cys Ala Leu Gln
            20                  25                  30

Ile Val Ala Arg Leu Lys Asn Asn Asn Arg Gln Val Cys Ile Asp Pro
        35                  40                  45

Lys Leu Lys Trp Ile Gln Glu Tyr Leu Glu Lys Ala Leu Asn
    50                  55                  60

<210> SEQ ID NO 7
<211> LENGTH: 67
<212> TYPE: PRT
<213> ORGANISM: Homo sapiens

<400> SEQUENCE: 7

Gly Tyr Ser Ser Asp Thr Thr Pro Cys Cys Phe Ala Tyr Ile Ala Arg
1               5                   10                  15

Pro Met Pro Arg Ala His Ile Lys Glu Tyr Phe Tyr Thr Ser Gly Lys
            20                  25                  30
```

```
Cys Ser Asn Pro Ala Val Val Phe Val Thr Arg Lys Asn Arg Gln Val
        35                  40                  45

Cys Ala Asn Pro Glu Lys Lys Trp Val Arg Glu Tyr Ile Asn Ser Leu
    50                  55                  60

Glu Met Ser
65

<210> SEQ ID NO 8
<211> LENGTH: 69
<212> TYPE: PRT
<213> ORGANISM: Homo sapiens

<400> SEQUENCE: 8

Ala Pro Met Gly Ser Asp Pro Pro Thr Ala Cys Cys Ala Ser Tyr Thr
1               5                   10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
    50                  55                  60

Asp Leu Glu Leu Asn
65

<210> SEQ ID NO 9
<211> LENGTH: 69
<212> TYPE: PRT
<213> ORGANISM: Homo sapiens

<400> SEQUENCE: 9

Ser Leu Ala Ala Asp Thr Pro Thr Ala Cys Cys Phe Ser Tyr Thr Ser
1               5                   10                  15

Arg Gln Ile Pro Gln Asn Phe Ile Ala Ala Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala
65

<210> SEQ ID NO 10
<211> LENGTH: 35
<212> TYPE: PRT
<213> ORGANISM: Human immunodeficiency virus type-1

<400> SEQUENCE: 10

Cys Thr Arg Pro Asn Asn Asn Thr Arg Lys Ser Ile Asn Ile Ala Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 11
<211> LENGTH: 35
<212> TYPE: PRT
<213> ORGANISM: Human immunodeficiency virus type-1
```

<400> SEQUENCE: 11

Cys Thr Arg Pro Asn Asn Asn Thr Arg Lys Ser Ile His Ile Gln Pro
1               5                   10                  15

Gly Arg Ala Phe Tyr Ala Thr Gly Glu Ile Ile Gly Asp Ile Arg Gln
            20                  25                  30

Ala His Cys
        35

<210> SEQ ID NO 12
<211> LENGTH: 35
<212> TYPE: PRT
<213> ORGANISM: Human immunodeficiency virus type-1

<400> SEQUENCE: 12

Cys Thr Arg Pro Asn Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 13
<211> LENGTH: 35
<212> TYPE: PRT
<213> ORGANISM: Human immunodeficiency virus type-1

<400> SEQUENCE: 13

Cys Thr Arg Pro Asn Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

<210> SEQ ID NO 14
<211> LENGTH: 35
<212> TYPE: PRT
<213> ORGANISM: Human immunodeficiency virus type-1

<400> SEQUENCE: 14

Cys Ile Arg Pro Asn Asn Asn Thr Arg Lys Ser Ile His Met Gly Pro
1               5                   10                  15

Gly Arg Ala Phe Tyr Ala Thr Gly Asp Ile Ile Gly Asn Ile Arg Gln
            20                  25                  30

Ala His Cys
        35

<210> SEQ ID NO 15
<211> LENGTH: 35
<212> TYPE: PRT
<213> ORGANISM: Human immunodeficiency virus type-1

<400> SEQUENCE: 15

Cys Val Arg Pro Asn Asn Asn Thr Arg Lys Ser Ile His Ile Gly Pro
1               5                   10                  15

Gly Gln Ala Phe Tyr Ala Thr Gly Asp Ile Ile Gly Asn Ile Arg Gln
            20                  25                  30

Ala His Cys
        35

```
<210> SEQ ID NO 16
<211> LENGTH: 35
<212> TYPE: PRT
<213> ORGANISM: Human immunodeficiency virus type-1

<400> SEQUENCE: 16

Cys Thr Arg Pro Asn Asn Asn Thr Arg Lys Ser Ile His Ile Gly Pro
1               5                   10                  15

Gly Gln Ala Phe Tyr Ala Thr Gly Asp Ile Ile Gly Asn Ile Arg Gln
            20                  25                  30

Ala His Cys
        35

<210> SEQ ID NO 17
<211> LENGTH: 35
<212> TYPE: PRT
<213> ORGANISM: Human immunodeficiency virus type-1

<400> SEQUENCE: 17

Cys Thr Arg Pro Asn Asn Asn Thr Arg Lys Ser Val His Ile Gly Pro
1               5                   10                  15

Gly Arg Ala Phe Tyr Gly Ile Gly Asp Ile Ile Gly Asn Ile Arg Gln
            20                  25                  30

Ala His Cys
        35

<210> SEQ ID NO 18
<211> LENGTH: 35
<212> TYPE: PRT
<213> ORGANISM: Human immunodeficiency virus type-1

<400> SEQUENCE: 18

Cys Thr Arg Pro Asn Asn Asn Thr Arg Lys Gly Val His Ile Gly Pro
1               5                   10                  15

Gly Arg Thr Phe Tyr Ala Thr Gly Glu Ile Ile Gly Asn Ile Arg Gln
            20                  25                  30

Ala His Cys
        35

<210> SEQ ID NO 19
<211> LENGTH: 35
<212> TYPE: PRT
<213> ORGANISM: Human immunodeficiency virus type-1

<400> SEQUENCE: 19

Cys Thr Arg Pro Asn Asn Asn Thr Arg Lys Gly Ile His Ile Gly Pro
1               5                   10                  15

Gly Arg Thr Phe Tyr Ala Thr Asp Ala Ile Ile Gly Asn Ile Arg Gln
            20                  25                  30

Ala His Cys
        35

<210> SEQ ID NO 20
<211> LENGTH: 35
<212> TYPE: PRT
<213> ORGANISM: Human immunodeficiency virus type-1

<400> SEQUENCE: 20

Cys Thr Arg Pro Asn Asn Asn Thr Arg Lys Gly Ile Asn Met Gly Pro
1               5                   10                  15
```

```
Gly Arg Ala Phe Tyr Ala Thr Thr Asp Ile Val Gly Asp Ile Ile Gln
            20                  25                  30

Ala His Cys
        35

<210> SEQ ID NO 21
<211> LENGTH: 35
<212> TYPE: PRT
<213> ORGANISM: Human immunodeficiency virus type-1

<400> SEQUENCE: 21

Cys Thr Arg Pro Asn Asn Asn Thr Arg Thr Gly Val His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 22
<211> LENGTH: 35
<212> TYPE: PRT
<213> ORGANISM: Human immunodeficiency virus type-1

<400> SEQUENCE: 22

Cys Ile Arg Pro Asn Asn Asn Thr Arg Lys Ser Ile Arg Ile Gly Pro
1               5                   10                  15

Gly Gln Ala Phe Tyr Ala Arg Gly Asp Val Ile Ser Asn Ile Arg His
            20                  25                  30

Ala Tyr Cys
        35

<210> SEQ ID NO 23
<211> LENGTH: 35
<212> TYPE: PRT
<213> ORGANISM: Human immunodeficiency virus type-1

<400> SEQUENCE: 23

Cys Ile Arg Pro Asn Asn Asn Thr Arg Lys Ser Ile His Ile Gly Pro
1               5                   10                  15

Gly Gln Ala Phe Tyr Ala Arg Gly Asp Ile Ile Gly Asn Ile Arg Gln
            20                  25                  30

Ala Tyr Cys
        35

<210> SEQ ID NO 24
<211> LENGTH: 35
<212> TYPE: PRT
<213> ORGANISM: Human immunodeficiency virus type-1

<400> SEQUENCE: 24

Cys Val Arg Pro Asn Asn Asn Thr Arg Arg Ser Ile His Ile Gly Pro
1               5                   10                  15

Gly Gln Ala Leu Tyr Ala Thr Gly Arg Ile Ile Gly Asn Ile Arg Gln
            20                  25                  30

Ala Tyr Cys
        35

<210> SEQ ID NO 25
<211> LENGTH: 35
<212> TYPE: PRT
<213> ORGANISM: Human immunodeficiency virus type-1
```

```
<400> SEQUENCE: 25

Cys Ile Arg Gly Asn Asn Thr Arg Lys Ser Met Arg Ile Gly Pro
1               5                   10                  15

Gly Gln Ala Phe Tyr Ala Thr Gly Asp Ile Ile Gly Asp Ile Arg Arg
            20                  25                  30

Ala Tyr Cys
        35

<210> SEQ ID NO 26
<211> LENGTH: 35
<212> TYPE: PRT
<213> ORGANISM: Human immunodeficiency virus type-1

<400> SEQUENCE: 26

Cys Ile Arg Gly Asn Asn Thr Arg Lys Ser Val Arg Ile Gly Pro
1               5                   10                  15

Gly Gln Thr Phe Tyr Thr His Gly Ala Ile Ile Gly Asp Ile Arg Gln
            20                  25                  30

Ala His Cys
        35

<210> SEQ ID NO 27
<211> LENGTH: 34
<212> TYPE: PRT
<213> ORGANISM: Human immunodeficiency virus type-1

<400> SEQUENCE: 27

Cys Thr Arg Pro Gly Asn Asn Thr Arg Arg Ser Ile Ser Ile Gly Pro
1               5                   10                  15

Gly Gln Ala Phe Tyr Thr Thr Asp Ile Ile Gly Asp Ile Arg Gln Ala
            20                  25                  30

Tyr Cys

<210> SEQ ID NO 28
<211> LENGTH: 35
<212> TYPE: PRT
<213> ORGANISM: Human immunodeficiency virus type-1

<400> SEQUENCE: 28

Cys Ile Arg Pro Asn Asn Asn Thr Arg Lys Ser Ile Pro Ile Gly Pro
1               5                   10                  15

Gly Arg Ala Phe Tyr Ala Thr Gly Asp Ile Ile Gly Asp Ile Arg Lys
            20                  25                  30

Ala Tyr Cys
        35

<210> SEQ ID NO 29
<211> LENGTH: 35
<212> TYPE: PRT
<213> ORGANISM: Human immunodeficiency virus type-1

<400> SEQUENCE: 29

Cys Ser Arg Pro Asn Asn Asn Thr Arg Lys Ser Ile His Ile Gly Pro
1               5                   10                  15

Gly Arg Ala Phe Tyr Ala Thr Asp Asp Ile Ile Gly Asn Ile Arg Gln
            20                  25                  30

Ala Tyr Cys
        35
```

<210> SEQ ID NO 30
<211> LENGTH: 35
<212> TYPE: PRT
<213> ORGANISM: Human immunodeficiency virus type-1

<400> SEQUENCE: 30

Cys Thr Arg Pro Gly Asn Asn Thr Arg Lys Ser Ile Arg Ile Gly Pro
1               5                   10                  15

Gly Gln Thr Phe Tyr Ala Thr Gly Asp Ile Ile Gly Asn Ile Arg Gln
            20                  25                  30

Ala His Cys
        35

<210> SEQ ID NO 31
<211> LENGTH: 35
<212> TYPE: PRT
<213> ORGANISM: Human immunodeficiency virus type-1

<400> SEQUENCE: 31

Cys Thr Arg Pro Gly Asn Asn Thr Arg Lys Ser Val Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 32
<211> LENGTH: 35
<212> TYPE: PRT
<213> ORGANISM: Human immunodeficiency virus type-1

<400> SEQUENCE: 32

Cys Thr Arg Pro Gly Ser Asn Thr Arg Lys Ser Ile Arg Ile Gly Pro
1               5                   10                  15

Gly Gln Ala Phe Tyr Ala Thr Gly Asp Val Ile Gly Asp Ile Arg Glu
            20                  25                  30

Ala Ser Cys
        35

<210> SEQ ID NO 33
<211> LENGTH: 35
<212> TYPE: PRT
<213> ORGANISM: Human immunodeficiency virus type-1

<400> SEQUENCE: 33

Cys Thr Arg Pro Gly Asn Asn Thr Arg Lys Ser Ile Arg Ile Gly Pro
1               5                   10                  15

Gly Gln Val Leu Tyr Ala Thr Gly Glu Ile Ile Gly Glu Ile Arg Gln
            20                  25                  30

Ala Tyr Cys
        35

<210> SEQ ID NO 34
<211> LENGTH: 35
<212> TYPE: PRT
<213> ORGANISM: Human immunodeficiency virus type-1

<400> SEQUENCE: 34

Cys Thr Arg Pro Asn Asn Asn Thr Arg Lys Ser Val Arg Ile Gly Pro
1               5                   10                  15

-continued

Gly Gln Thr Phe Tyr Ala Thr Gly Asp Ile Ile Gly Glu Ile Arg Gln
            20                  25                  30

Ala Tyr Cys
        35

<210> SEQ ID NO 35
<211> LENGTH: 35
<212> TYPE: PRT
<213> ORGANISM: Human immunodeficiency virus type-1

<400> SEQUENCE: 35

Cys Thr Arg Pro Asn Asn Asn Thr Arg Glu Ser Val Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 36
<211> LENGTH: 35
<212> TYPE: PRT
<213> ORGANISM: Human immunodeficiency virus type-1

<400> SEQUENCE: 36

Cys Thr Arg Pro Asn Asn Asn Thr Arg Arg Ser Ile Gly Ile Gly Pro
1               5                   10                  15

Gly Gln Thr Ile Tyr Ala Thr Gly Ala Ile Ile Gly Asp Ile Arg Gln
            20                  25                  30

Ala His Cys
        35

<210> SEQ ID NO 37
<211> LENGTH: 35
<212> TYPE: PRT
<213> ORGANISM: Human immunodeficiency virus type-1

<400> SEQUENCE: 37

Cys Thr Arg Pro Ser Asn Asn Thr Arg Lys Gly Trp His Ile Gly Pro
1               5                   10                  15

Gly Gln Thr Leu Tyr Ala Thr Gly Ala Ile Ile Gly Asp Ile Arg Gln
            20                  25                  30

Ala His Cys
        35

<210> SEQ ID NO 38
<211> LENGTH: 35
<212> TYPE: PRT
<213> ORGANISM: Human immunodeficiency virus type-1

<400> SEQUENCE: 38

Cys Thr Arg Pro Asn Asn Asn Thr Arg Lys Ser Ile Arg Ile Gly Pro
1               5                   10                  15

Gly Gln Ala Leu Tyr Ala Thr Gly Ala Ile Ile Gly Asn Ile Arg Gln
            20                  25                  30

Ala His Cys
        35

<210> SEQ ID NO 39
<211> LENGTH: 35
<212> TYPE: PRT
<213> ORGANISM: Human immunodeficiency virus type-1

```
<400> SEQUENCE: 39

Cys Thr Arg Pro Asn Asn Thr Arg Lys Ser Ile Gly Ile Gly Pro
1               5                   10                  15

Gly Gln Val Phe Tyr Ala Thr Gly Asp Ile Ile Gly Asp Ile Arg Gln
            20                  25                  30

Ala His Cys
        35

<210> SEQ ID NO 40
<211> LENGTH: 35
<212> TYPE: PRT
<213> ORGANISM: Human immunodeficiency virus type-1

<400> SEQUENCE: 40

Cys Thr Arg Pro Gly Asn Asn Thr Arg Lys Gly Ile Gly Ile Gly Pro
1               5                   10                  15

Gly Gln Met Phe Tyr Ala Thr Gly Ser Ile Ile Gly Asp Ile Arg Gln
            20                  25                  30

Ala His Cys
        35

<210> SEQ ID NO 41
<211> LENGTH: 35
<212> TYPE: PRT
<213> ORGANISM: Human immunodeficiency virus type-1

<400> SEQUENCE: 41

Cys Thr Arg Pro Asn Asn Thr Arg Arg Ser Ile Pro Met Gly Pro
1               5                   10                  15

Gly Lys Ala Phe Tyr Ala Thr Gly Asp Ile Ile Gly Asp Ile Arg Gln
            20                  25                  30

Ala His Cys
        35

<210> SEQ ID NO 42
<211> LENGTH: 35
<212> TYPE: PRT
<213> ORGANISM: Human immunodeficiency virus type-1

<400> SEQUENCE: 42

Cys Thr Arg Pro Ser Asn Asn Thr Arg Lys Ser Ile Pro Ile Gly Pro
1               5                   10                  15

Gly Gln Ala Ile Tyr Ala Thr Gly Glu Ile Ile Gly Asp Ile Arg Lys
            20                  25                  30

Ala His Cys
        35

<210> SEQ ID NO 43
<211> LENGTH: 35
<212> TYPE: PRT
<213> ORGANISM: Human immunodeficiency virus type-1

<400> SEQUENCE: 43

Cys Thr Arg Pro Asn Asn Thr Arg Lys Ser Ile His Met Gly Pro
1               5                   10                  15

Gly Gln Ala Met Tyr Val Thr Gly Asp Ile Ile Gly Asp Ile Arg Arg
            20                  25                  30

Ala His Cys
        35
```

<210> SEQ ID NO 44
<211> LENGTH: 35
<212> TYPE: PRT
<213> ORGANISM: Human immunodeficiency virus type-1

<400> SEQUENCE: 44

Cys Thr Arg Pro Asn Asn Asn Thr Arg Glu Ser Ile Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 45
<211> LENGTH: 35
<212> TYPE: PRT
<213> ORGANISM: Human immunodeficiency virus type-1

<400> SEQUENCE: 45

Cys Thr Arg Pro Asn Asn Asn Thr Arg Lys Ser Ile Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 46
<211> LENGTH: 35
<212> TYPE: PRT
<213> ORGANISM: Human immunodeficiency virus type-1

<400> SEQUENCE: 46

Cys Thr Arg Pro Asn Asn Asn Thr Arg Lys Ser Ile Arg Ile Gly Pro
1               5                   10                  15

Gly Gln Val Phe Tyr Ala Thr Gly Asp Ile Ile Gly Asp Ile Arg Gln
            20                  25                  30

Ala His Cys
        35

<210> SEQ ID NO 47
<211> LENGTH: 35
<212> TYPE: PRT
<213> ORGANISM: Human immunodeficiency virus type-1

<400> SEQUENCE: 47

Cys Ile Arg Pro Asn Asn Asn Thr Arg Lys Ser Val Arg Ile Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 48
<211> LENGTH: 35
<212> TYPE: PRT
<213> ORGANISM: Human immunodeficiency virus type-1

<400> SEQUENCE: 48

Cys Val Arg Pro Ser Asn Asn Thr Arg Lys Ser Ile Arg Ile Gly Pro
1               5                   10                  15

Gly Gln Thr Phe Tyr Ala Thr Gly Asp Ile Thr Gly Asp Ile Arg Gln
            20                  25                  30

Ala His Cys
        35

<210> SEQ ID NO 49
<211> LENGTH: 34
<212> TYPE: PRT
<213> ORGANISM: Human immunodeficiency virus type-1

<400> SEQUENCE: 49

Cys Thr Arg Pro Ser Asn Asn Thr Arg Gln Gly Ile His Ile Gly Pro
1               5                   10                  15

Gly Gln Ala Leu Tyr Thr Thr Lys Ile Ile Gly Asp Ile Arg Gln Ala
            20                  25                  30

His Cys

<210> SEQ ID NO 50
<211> LENGTH: 35
<212> TYPE: PRT
<213> ORGANISM: Human immunodeficiency virus type-1

<400> SEQUENCE: 50

Cys Thr Arg Pro Asn Asn Asn Thr Arg Lys Ser Ile His Ile Gly Pro
1               5                   10                  15

Gly Gln Ala Phe Tyr Ala Ile Gly Asp Val Ile Gly Asn Ile Arg Gln
            20                  25                  30

Ala Gln Cys
        35

<210> SEQ ID NO 51
<211> LENGTH: 35
<212> TYPE: PRT
<213> ORGANISM: Human immunodeficiency virus type-1

<400> SEQUENCE: 51

Cys Ile Arg Pro Asn Asn Asn Thr Arg Lys Ser Val His Ile Gly Pro
1               5                   10                  15

Gly Gln Thr Phe Tyr Ala Thr Gly Asp Ile Ile Gly Asn Ile Arg Gln
            20                  25                  30

Ala His Cys
        35

<210> SEQ ID NO 52
<211> LENGTH: 35
<212> TYPE: PRT
<213> ORGANISM: Human immunodeficiency virus type-1

<400> SEQUENCE: 52

Cys Thr Arg Pro Asn Asn Asn Thr Arg Lys Arg Ile His Ile Gly Pro
1               5                   10                  15

Gly Arg Ala Phe Tyr Thr Thr Gly Gln Ile Ile Gly Asn Ile Arg Gln
            20                  25                  30

Ala Tyr Cys
        35

<210> SEQ ID NO 53
<211> LENGTH: 35
<212> TYPE: PRT
<213> ORGANISM: Human immunodeficiency virus type-1

-continued

```
<400> SEQUENCE: 53

Cys Thr Arg Pro Asn Asn Thr Arg Lys Arg Ile His Ile Gly Pro
1               5                   10                  15

Gly Arg Ala Phe Tyr Thr Thr Gly Gln Ile Ile Gly Asn Ile Arg Gln
            20                  25                  30

Ala His Cys
        35

<210> SEQ ID NO 54
<211> LENGTH: 35
<212> TYPE: PRT
<213> ORGANISM: Human immunodeficiency virus type-1

<400> SEQUENCE: 54

Cys Thr Arg Pro Asn Asn Thr Arg Lys Arg Ile His Ile Gly Pro
1               5                   10                  15

Gly Arg Ala Phe His Thr Thr Gly Ala Ile Ile Gly Lys Ile Arg Gln
            20                  25                  30

Ala His Cys
        35

<210> SEQ ID NO 55
<211> LENGTH: 35
<212> TYPE: PRT
<213> ORGANISM: Human immunodeficiency virus type-1

<400> SEQUENCE: 55

Cys Thr Arg Pro Asn Asn Thr Arg Lys Arg Ile His Ile Gly Pro
1               5                   10                  15

Gly Arg Ala Phe Tyr Thr Thr Gly Gly Ile Ile Gly Asn Ile Arg Gln
            20                  25                  30

Ala His Cys
        35

<210> SEQ ID NO 56
<211> LENGTH: 35
<212> TYPE: PRT
<213> ORGANISM: Human immunodeficiency virus type-1

<400> SEQUENCE: 56

Cys Thr Arg Pro Asn Asn Thr Arg Lys Arg Ile His Ile Gly Pro
1               5                   10                  15

Gly Arg Ala Phe Tyr Ala Thr Gly Lys Ile Ile Gly Asp Ile Arg Gln
            20                  25                  30

Ala His Cys
        35

<210> SEQ ID NO 57
<211> LENGTH: 35
<212> TYPE: PRT
<213> ORGANISM: Human immunodeficiency virus type-1

<400> SEQUENCE: 57

Cys Ile Arg Pro Asn Asn Thr Arg Arg Arg Ile His Ile Gly Pro
1               5                   10                  15

Gly Arg Ala Phe Tyr Ala Thr Gly Arg Ile Ile Gly Asn Ile Arg Gln
            20                  25                  30

Ala Tyr Cys
        35
```

<210> SEQ ID NO 58
<211> LENGTH: 35
<212> TYPE: PRT
<213> ORGANISM: Human immunodeficiency virus type-1

<400> SEQUENCE: 58

Cys Ile Arg Pro Asn Asn Asn Thr Arg Arg Ser Ile His Ile Gly Pro
1               5                   10                  15

Gly Arg Ala Phe Tyr Ala Thr Gly Arg Ile Ile Gly Asp Ile Arg Arg
            20                  25                  30

Ala Tyr Cys
        35

<210> SEQ ID NO 59
<211> LENGTH: 35
<212> TYPE: PRT
<213> ORGANISM: Human immunodeficiency virus type-1

<400> SEQUENCE: 59

Cys Ile Arg Pro Asn Asn Asn Thr Arg Thr Lys Ile Arg Ile Gly Pro
1               5                   10                  15

Gly Gln Ala Phe Tyr Ala Thr Gly Asn Ile Ile Gly Asp Ile Arg Gln
            20                  25                  30

Ala Tyr Cys
        35

<210> SEQ ID NO 60
<211> LENGTH: 35
<212> TYPE: PRT
<213> ORGANISM: Human immunodeficiency virus type-1

<400> SEQUENCE: 60

Cys Leu Arg Pro Asn Asn Asn Thr Arg Lys Arg Ile His Leu Gly Pro
1               5                   10                  15

Gly Arg Ala Phe Tyr Ala Ala Gly Glu Ile Ile Gly Lys Ile Arg Gln
            20                  25                  30

Ala His Cys
        35

<210> SEQ ID NO 61
<211> LENGTH: 35
<212> TYPE: PRT
<213> ORGANISM: Human immunodeficiency virus type-1

<400> SEQUENCE: 61

Cys Thr Arg Pro Asn Asn Asn Ile Arg Arg Ile His Ile Gly Pro
1               5                   10                  15

Gly Arg Ala Phe Tyr Ala Thr Gly Asp Ile Ile Gly Asp Ile Arg Lys
            20                  25                  30

Ala Tyr Cys
        35

<210> SEQ ID NO 62
<211> LENGTH: 35
<212> TYPE: PRT
<213> ORGANISM: Human immunodeficiency virus type-1

<400> SEQUENCE: 62

Cys Thr Arg Pro Asn Asn Asn Thr Arg Arg Arg Ile His Ile Gly Pro
1               5                   10                  15

-continued

```
Gly Arg Ala Phe Tyr Ala Thr Gly Asp Thr Ile Gly Asp Ile Arg Lys
            20                  25                  30

Ala Tyr Cys
        35

<210> SEQ ID NO 63
<211> LENGTH: 35
<212> TYPE: PRT
<213> ORGANISM: Human immunodeficiency virus type-1

<400> SEQUENCE: 63

Cys Thr Arg Pro Asn Asp Asn Ile Arg Lys Arg Val His Ile Gly Pro
1               5                   10                  15

Gly Gln Ala Phe Tyr Ala Thr Gly Asp Val Ile Gly Asp Ile Arg Arg
            20                  25                  30

Ala His Cys
        35

<210> SEQ ID NO 64
<211> LENGTH: 35
<212> TYPE: PRT
<213> ORGANISM: Human immunodeficiency virus type-1

<400> SEQUENCE: 64

Cys Thr Arg Pro Asn Asn Asn Ile Arg Arg Ile His Ile Gly Pro
1               5                   10                  15

Gly Arg Ala Phe Tyr Ala Thr Gly Gly Ile Arg Gly Asp Ile Arg Lys
            20                  25                  30

Ala Tyr Cys
        35

<210> SEQ ID NO 65
<211> LENGTH: 35
<212> TYPE: PRT
<213> ORGANISM: Human immunodeficiency virus type-1

<400> SEQUENCE: 65

Cys Thr Arg Pro Asn Asn Asn Ile Arg Arg Ile Arg Ile Gly Pro
1               5                   10                  15

Gly Arg Ala Tyr Phe Thr Arg Gly Gln Ile Lys Glu His Met Arg Lys
            20                  25                  30

Ala His Cys
        35

<210> SEQ ID NO 66
<211> LENGTH: 35
<212> TYPE: PRT
<213> ORGANISM: Human immunodeficiency virus type-1

<400> SEQUENCE: 66

Cys Thr Arg Pro Ser Asn Asn Thr Arg Lys Arg Ile Pro Ile Gly Pro
1               5                   10                  15

Arg Arg Ala Phe Tyr Ala Thr Gly Asp Ile Val Gly Asp Ile Arg Arg
            20                  25                  30

Ala His Cys
        35

<210> SEQ ID NO 67
<211> LENGTH: 35
<212> TYPE: PRT
```

<213> ORGANISM: Human immunodeficiency virus type-1

<400> SEQUENCE: 67

Cys Thr Arg Pro Asn Asn His Thr Arg Lys Arg Met Thr Leu Gly Pro
1 5 10 15

Gly Arg Val Tyr Tyr Thr Thr Gly Glu Ile Leu Gly Asp Ile Lys Lys
20 25 30

Ala His Cys
35

<210> SEQ ID NO 68
<211> LENGTH: 35
<212> TYPE: PRT
<213> ORGANISM: Human immunodeficiency virus type-1

<400> SEQUENCE: 68

Cys Thr Arg Pro Asn Asn His Thr Arg Lys Arg Met Thr Leu Gly Pro
1 5 10 15

Gly Lys Val Tyr Tyr Thr Thr Gly Glu Ile Val Gly Asp Ile Lys Lys
20 25 30

Ala His Cys
35

<210> SEQ ID NO 69
<211> LENGTH: 35
<212> TYPE: PRT
<213> ORGANISM: Human immunodeficiency virus type-1

<400> SEQUENCE: 69

Cys Thr Arg Pro Asn Asn His Thr Arg Lys Arg Ile Ser Leu Gly Pro
1 5 10 15

Gly Arg Ala Tyr Tyr Thr Thr Gly Glu Ile Val Gly Ser Ile Lys Lys
20 25 30

Ala His Cys
35

<210> SEQ ID NO 70
<211> LENGTH: 35
<212> TYPE: PRT
<213> ORGANISM: Human immunodeficiency virus type-1

<400> SEQUENCE: 70

Cys Thr Arg Pro Asn Asn Asn Thr Arg Lys Arg Ile Arg Ile Gly Pro
1 5 10 15

Gly Arg Ala Val Tyr Thr Thr Gly Lys Ile Ile Gly Lys Ile Arg Gln
20 25 30

Ala His Cys
35

<210> SEQ ID NO 71
<211> LENGTH: 35
<212> TYPE: PRT
<213> ORGANISM: Human immunodeficiency virus type-1

<400> SEQUENCE: 71

Cys Thr Arg Pro Asn Thr Asn Lys Arg Lys Arg Thr Thr Lys Gly Pro
1 5 10 15

Gly Arg Val Ile Tyr Ala Thr Gly Gln Ile Ile Gly Lys Ile Arg Gln
20 25 30

Ala His Cys

35

<210> SEQ ID NO 72
<211> LENGTH: 35
<212> TYPE: PRT
<213> ORGANISM: Human immunodeficiency virus type-1

<400> SEQUENCE: 72

Cys Thr Arg Pro Asn Asn Asn Thr Arg Lys Arg Ile Ser Ile Gly Pro
1               5                   10                  15

Gly Arg Ala Phe Tyr Thr Thr Gly Gln Ile Ile Gly Asn Ile Arg Gln
            20                  25                  30

Ala His Cys
        35

<210> SEQ ID NO 73
<211> LENGTH: 35
<212> TYPE: PRT
<213> ORGANISM: Human immunodeficiency virus type-1

<400> SEQUENCE: 73

Cys Thr Arg Pro Asn Asn Asn Thr Arg Lys Arg Ile Ser Ile Gly Pro
1               5                   10                  15

Gly Arg Ala Phe Tyr Thr Ile Gly Gln Ile Ile Gly Asn Ile Arg Gln
            20                  25                  30

Ala His Cys
        35

<210> SEQ ID NO 74
<211> LENGTH: 35
<212> TYPE: PRT
<213> ORGANISM: Human immunodeficiency virus type-1

<400> SEQUENCE: 74

Cys Thr Arg Pro Asn Asn Asn Thr Arg Lys Gly Ile Ser Val Gly Pro
1               5                   10                  15

Gly Arg Ala Ile Tyr Ala Thr Lys Asn Ile Ile Gly Asp Ile Ser Gln
            20                  25                  30

Ala His Cys
        35

<210> SEQ ID NO 75
<211> LENGTH: 35
<212> TYPE: PRT
<213> ORGANISM: Human immunodeficiency virus type-1

<400> SEQUENCE: 75

Cys Thr Arg Pro Lys Asn Asn Thr Arg Lys Pro Ile His Ile Gly Pro
1               5                   10                  15

Gly Arg Ala Phe Tyr Ala Thr Arg Glu Ile Arg Gly Asn Ile Ile Gln
            20                  25                  30

Ala His Cys
        35

<210> SEQ ID NO 76
<211> LENGTH: 35
<212> TYPE: PRT
<213> ORGANISM: Human immunodeficiency virus type-1

<400> SEQUENCE: 76

Cys Thr Arg Pro Asn Asn Asn Thr Arg Lys Arg Ile Ser Val Gly Pro

```
1               5                   10                  15
Gly Arg Ala Phe Tyr Ala Thr Gly Asn Ile Ile Gly Lys Ile Ser Gln
            20                  25                  30

Ala His Cys
        35

<210> SEQ ID NO 77
<211> LENGTH: 35
<212> TYPE: PRT
<213> ORGANISM: Human immunodeficiency virus type-1

<400> SEQUENCE: 77

Cys Thr Arg Pro Asn Asn Asn Thr Arg Lys Arg Ile Arg Ile Gly Pro
1               5                   10                  15

Gly Arg Ala Phe Tyr Thr Thr Gly Gln Ile Ile Gly Asp Ile Arg Gln
            20                  25                  30

Ala His Cys
        35

<210> SEQ ID NO 78
<211> LENGTH: 35
<212> TYPE: PRT
<213> ORGANISM: Human immunodeficiency virus type-1

<400> SEQUENCE: 78

Cys Thr Arg Pro Asn Asn Asn Thr Ile Thr Arg Ile Arg Ile Gly Pro
1               5                   10                  15

Gly Gln Ala Phe Tyr Ala Thr Gly Ser Ile Ile Gly Asn Ile Arg Gln
            20                  25                  30

Ala His Cys
        35

<210> SEQ ID NO 79
<211> LENGTH: 37
<212> TYPE: PRT
<213> ORGANISM: Human immunodeficiency virus type-1

<400> SEQUENCE: 79

Cys Ser Arg Pro Tyr Lys Lys Glu Arg Gln Arg Thr His Ile Gly Pro
1               5                   10                  15

Gly Gln Ala Leu Tyr Thr Thr Arg Thr Thr Arg Val Glu Gly Asn Ile
            20                  25                  30

Arg Gln Ala His Cys
        35

<210> SEQ ID NO 80
<211> LENGTH: 35
<212> TYPE: PRT
<213> ORGANISM: Human immunodeficiency virus type-1

<400> SEQUENCE: 80

Cys Val Arg Pro Tyr Arg Asn Ile Lys Ile Gln Arg Thr Pro Ile Gly
1               5                   10                  15

Leu Gly Gln Ala Leu Tyr Thr Thr Lys Arg Ile Gly His Ile Gly Gln
            20                  25                  30

Ala His Cys
        35

<210> SEQ ID NO 81
<211> LENGTH: 35
```

```
<212> TYPE: PRT
<213> ORGANISM: Artificial Sequence
<220> FEATURE:
<223> OTHER INFORMATION: Human immunodeficiency virus type-1 R5
      consensus sequence
<220> FEATURE:
<221> NAME/KEY: MISC_FEATURE
<222> LOCATION: (10)..(10)
<223> OTHER INFORMATION: The Xaa at position 10 may be any amino acid
<220> FEATURE:
<221> NAME/KEY: MISC_FEATURE
<222> LOCATION: (12)..(12)
<223> OTHER INFORMATION: The Xaa at position 12 may be any amino acid
<220> FEATURE:
<221> NAME/KEY: MISC_FEATURE
<222> LOCATION: (13)..(13)
<223> OTHER INFORMATION: The Xaa at position 13 may be any amino acid
<220> FEATURE:
<221> NAME/KEY: MISC_FEATURE
<222> LOCATION: (18)..(18)
<223> OTHER INFORMATION: The Xaa at position 18 may be any amino acid
<220> FEATURE:
<221> NAME/KEY: MISC_FEATURE
<222> LOCATION: (19)..(19)
<223> OTHER INFORMATION: The Xaa at position 19 may be any amino acid
<220> FEATURE:
<221> NAME/KEY: MISC_FEATURE
<222> LOCATION: (20)..(20)
<223> OTHER INFORMATION: The Xaa at position 20 may be any amino acid
<220> FEATURE:
<221> NAME/KEY: MISC_FEATURE
<222> LOCATION: (20)..(20)
<223> OTHER INFORMATION: The Xaa at position 20 may be any amino acid
<220> FEATURE:
<221> NAME/KEY: MISC_FEATURE
<222> LOCATION: (34)..(34)
<223> OTHER INFORMATION: The Xaa at position 34 may be any amino acid

<400> SEQUENCE: 81

Cys Thr Arg Pro Asp Asn Asn Thr Arg Xaa Thr Xaa Xaa Ile Gly Pro
  1               5                  10                  15

Gly Xaa Xaa Xaa Tyr Ala Thr Gly Asp Ile Ile Gly Asp Ile Arg Gln
             20                  25                  30

Ala Xaa Cys
        35

<210> SEQ ID NO 82
<211> LENGTH: 38
<212> TYPE: PRT
<213> ORGANISM: Artificial Sequence
<220> FEATURE:
<223> OTHER INFORMATION: Human immunodeficiency virus type-1 X4
      consensus sequence
<220> FEATURE:
<221> NAME/KEY: MISC_FEATURE
<222> LOCATION: (10)..(10)
<223> OTHER INFORMATION: The Xaa at position 10 is Ile or may not be
      present
<220> FEATURE:
<221> NAME/KEY: MISC_FEATURE
<222> LOCATION: (11)..(11)
<223> OTHER INFORMATION: The Xaa at position 11 may be any amino acid
<220> FEATURE:
<221> NAME/KEY: MISC_FEATURE
<222> LOCATION: (14)..(14)
<223> OTHER INFORMATION: The Xaa at position 14 may be any amino acid
<220> FEATURE:
<221> NAME/KEY: MISC_FEATURE
<222> LOCATION: (15)..(15)
<223> OTHER INFORMATION: The Xaa at position 15 may be any amino acid
<220> FEATURE:
<221> NAME/KEY: MISC_FEATURE
<222> LOCATION: (21)..(21)
<223> OTHER INFORMATION: The Xaa at position 21 may be any amino acid
<220> FEATURE:
```

```
-continued

<221> NAME/KEY: MISC_FEATURE
<222> LOCATION: (23)..(23)
<223> OTHER INFORMATION: The Xaa at position 23 may be any amino acid
<220> FEATURE:
<221> NAME/KEY: MISC_FEATURE
<222> LOCATION: (25)..(25)
<223> OTHER INFORMATION: The Xaa at position 26 may be any amino acid
<220> FEATURE:
<221> NAME/KEY: MISC_FEATURE
<222> LOCATION: (28)..(28)
<223> OTHER INFORMATION: The Xaa at position 28 may be any amino acid
<220> FEATURE:
<221> NAME/KEY: MISC_FEATURE
<222> LOCATION: (29)..(29)
<223> OTHER INFORMATION: The Xaa at position 29 is Val or may not be
      present
<220> FEATURE:
<221> NAME/KEY: MISC_FEATURE
<222> LOCATION: (30)..(30)
<223> OTHER INFORMATION: The Xaa at position 30 is Glu or may not be
      present
<220> FEATURE:
<221> NAME/KEY: MISC_FEATURE
<222> LOCATION: (34)..(34)
<223> OTHER INFORMATION: The Xaa at position 34 may be any amino acid
<220> FEATURE:
<221> NAME/KEY: MISC_FEATURE
<222> LOCATION: (35)..(35)
<223> OTHER INFORMATION: The Xaa at position 35 may be any amino acid
<220> FEATURE:
<221> NAME/KEY: MISC_FEATURE
<222> LOCATION: (37)..(37)
<223> OTHER INFORMATION: The Xaa at position 37 may be any amino acid

<400> SEQUENCE: 82

Cys Thr Arg Pro Asn Asn Asn Thr Arg Xaa Xaa Arg Ile Xaa Xaa Gly
1               5                   10                  15

Pro Gly Arg Ala Xaa Tyr Xaa Thr Gly Xaa Ile Xaa Xaa Xaa Gly Asp
            20                  25                  30

Ile Xaa Xaa Ala Xaa Cys
        35
```

METHOD FOR DETERMINING CO-RECEPTOR SELECTIVITY OF HUMAN IMMUNODEFICIENCY VIRUS-1

PRIORITY

This application claims priority from U.S. Provisional Application Ser. No. 60/658,574 filed on Mar. 07, 2005.

STATEMENT OF RIGHTS TO INVENTIONS MADE UNDER FEDERALLY SPONSORED RESEARCH

This invention was funded in part by grants from the National Institute of Health, and from the Department of Veterans Affairs, which provides to the United States government certain rights in this invention.

BACKGROUND OF THE INVENTION

1. Field of the Invention

The present invention in the fields of structural biology, immunology and medicine relates to a newly discovered structural characteristic of the gp120 V3 loop and a resultant "rule" or algorithm, that is used in a method for determining whether a subject is infected with Human Immunodeficiency Virus-1 (HIV-1) that expresses selectivity for CXCR4 (or CCR5) chemokine receptors. A positively charged surface patch defined by V3 loop residues 11 and 24 or 25 at the base of the β-strands in the V3 loop and the homologous β2-β3 chemokine hairpin is responsible for CXCR4 receptor selection.

2. Description of the Background Art

A substantial library of structural data has accumulated describing the major surface protein of HIV-1, gp120. gp120 requires interaction with CD4 and chemokine receptors on the surface of target cells in order for HIV-1 to infect cells. The third variable loop (V3) of gp120 is one of the critical HIV-1 regions responsible for initial interaction of gp120 with host cells. The V3 loop interacts with the chemokine receptors [1, 2], and specific V3 residues dictate the choice of co-receptor usage [3-14]. (Numbers appearing between square brackets "[ ]" refer to the numbering of references cited in a list prior to the claims.) HIV-1 co-receptor usage plays a critical role in viral tropism, transmission, and disease progression in infected individuals [15, 16]. Deletion of the V3 loop abolishes virus infectivity [17-19], and replacement of the V3 loop with a portion of the CXC chemokine SDF-1 preserves infectivity [20]. In addition, several human monoclonal antibodies (mAbs) specific for the V3 loop, derived from the cells of HIV-1-infected patients, are broadly neutralizing [21-24], and immunization of animals with proteins into which the V3 loop has been inserted results in HIV-1 neutralizing antibodies [25, 26]. All of these well-documented findings provide evidence that the V3 loop plays a critical role through direct protein-protein interactions in virus infectivity. In addition, X-ray and NMR studies have confirmed that different V3 loops are able to adopt the same overall 3D structure: a β-hairpin [27-33]. Thus, different V3 loops exhibit common protein structural characteristics, and the V3 loop represents a functionally important region of the virus envelope, despite its well-described variation in sequence.

HIV-1 strains that require the CXCR4 co-receptor on target cells for infection are termed "X4"-tropic viruses; those requiring the CCR5 co-receptor are termed "R5"-tropic; those able to utilize both are termed "dual-tropic." Co-receptor utilization has often been predicted using HIV-1 envelope sequence information, resulting in assignment of viral tropism, or "phenotype", on the basis of the V3 loop sequence. This prediction has turned out to be less accurate for X4 than for R5 viruses (Resch et al. [35] and is confounded by the use of genotypic analyses in different studies of viral quasi-species or molecular clones. Further confusion results from historical nomenclature because the term "tropism" was originally associated with viral growth characteristics. It is now appreciated, however, that the original designations ("slow/low" vs. "rapid/high" and non-syncytium-inducing (NSI) vs. syncytium-inducing (SI)) do not always correlate with co-receptor usage (E M Fenyö et al., *J. Virol.*, 62:4414, 1988; M. Tersmette, *J Virol.* 63:2118, 1989; P. Zhong et al. [77]. Thus, any structure/function analysis of HIV-1 tropism must be based on a panel of viruses with carefully defined co-receptor usage.

Mutational data suggested that two positions in V3 sequences were the primary determinants of HIV-1 tropism for X4, as opposed to R5, co-receptors: Mutation of the negatively charged residue at position "25" (based on numbering of the V3 loop in the consensus sequence of HIV-1 subtype B beginning with the N-terminal Cys assigned position 1, i.e.,

*C*TRPNNNTRK*S*IHIGPGRAFYTTG*E*IIGDIRQAHC    [SEQ ID NO:1]

where residues 1 and 25 are shown in bold-face, italics), to a positively charged residue changes the tropism of an R5 virus to that of an X4 virus [10]. Conversely, a negatively charged residue may be accommodated at position 25 in an X4 virus if a positively charged residue is present at the "11" position (underlined above).

These findings gave rise to the so-called "11/25 rule" [3, 10, 13, 34]. According to this rule, if a positive charge is present at position 11 or 25 of the V3 loop sequence, the virus is predicted to be X4-tropic. However, this scheme is not truly a "rule" because of its low predictive accuracy. Additional "rules" have been promulgated in attempts to decipher the basis of receptor tropism through sequence alone, but the best performing algorithms could achieve only about 70% predictive accuracy [13, 35, 36]. Moreover, these computational studies did not rely upon a "gold standard test set" of V3 sequences with exclusive CCR5 or CXCR4 selectivity that were directly verified by assays of co-receptor usage. Finally, the mechanism by which these amino acid substitutions produce a change in tropism remains unknown.

The mechanism of tropism might be better appreciated if the structure of the V3 loop, including the positioning in space of residues 11 and 25, could be observed. Unfortunately, the V3 loop is characterized by structural disorder such that its deletion has been required for crystallographic resolution of gp120 structure [37, 38]. This characteristic has made experimental determination of the native V3 loop structure difficult. The structural variation associated with such disorder, from a statistical mechanics point of view, may range from a complete absence of order (very little chance that any give structural conformation exists at any given time) to a strong, albeit not complete, preference for a single conformation [39]. However, it is often true that "natural" structural disorder in proteins favors a particular conformation in the right environment [40]. In the case of the V3 loop, this favored conformation may be both biologically important and biologically vulnerable.

Ordered structures of the V3 loop in complex with neutralizing mAbs have been resolved by both X-ray crystallography NMR spectroscopy [27-29, 41-44]. Given the neutralizing activities of these mAbs, it may be inferred that the structural conformation of V3 present in the V3/mAb complexes are the same as those that occur when the native virus interacts with the chemokine receptors. Moreover, structural details of the V3 loop in complex with mAbs that neutralize R5- and X4-tropic viruses have recently been obtained. Notably, these structures include the "11" position but not the "25" position of V3. However, the extent of structural detail is adequate to offer insights into how different viral V3 sequences dictate the recognition of different chemokine receptors.

The central portion of the V3 loop is a β-hairpin fold (strand-turn/loop-strand) the N-terminal strand of which makes most of the binding contact with neutralizing antibodies [28, 29]. In the only crystallographic structure of a V3 peptide in complex with an R5-neutralizing human mAb, the N-terminal strand exhibits one specific electrostatic contact (at position 18), but most of the interaction with the antibody is through backbone and non-specific side chain contacts of antibody atoms with the V3 β-hairpin's N-terminal strand [29]. Thus, conservation of the β-hairpin structure may be required to preserve this antigen/antibody interaction. However, since the side chains in a β-strand point in a perpendicular direction from the plane of the β-strand, and the broadly neutralizing mAb studied recognizes primarily main chain and hydrophobic side-chain atoms of the β-strand, a great deal of sequence variation is afforded without impact on the observed binding mode, explaining the broadly neutralizing capacity of the mAb. Indeed, the sequence of this region of the V3 loop is known to be extremely variable [45]. Thus, the crystallographic and NMR data may explain why some sequence variability of the V3 loop may be inconsequential to chemokine receptor binding and to recognition by certain antibodies.

The natural ligands of the HIV-1 co-receptors are chemokines, and the classification of chemokine receptors is based on the grouping of these chemokines. For example, CXCR4 is the receptor for the CXC chemokines (e.g., SDF-1) and CCR5 is a receptor for several CC chemokines (RANTES, MIP-1α and MIP-1β). Chemokines contain a central β-sheet and C-terminal β-helical structural features [46]. Interestingly, a structural homology is evident between the β2-β3 hairpin of both groups of chemokines and the β-hairpin of the V3 loop: The homology "segregates" with biological activity such that (1) an homology exists between the structure of the V3 loop when in complex with an X4-neutralizing antibody and the β2-β3 hairpin in SDF-1, whereas (2) a parallel homology exists between the structure of the V3 loop when in complex with an R5-neutralizing antibody and the β2-β3 hairpin in RANTES, MIP-1α and MIP-1β [28].

Mutational analysis of the chemokines has revealed that a cluster of residues (the "N-loop") located on the surface of chemokine MIP-1β near the base of the β2-β3 hairpin is one of the important sites for receptor binding [47]. Moreover, as an impetus for the present study, the present inventors noticed, that two residues in or near the β2 and β3 strands that are close to the N-loop in 3D space may align with the so-called "11" and "25" residues of the V3 loop which play a critical role in determining chemokine receptor selection. The inventors therefore used the known 3D structures of the chemokines and of the V3 loops of both R5 and X4 viruses, along with a library of V3 loop sequences from primary HIV-1 strains with confirmed (and exclusive) CXCR4 or CCR5 usage, to elucidate the structure/function relationships that determine chemokine receptor selectivity and therefore HIV-1 tropism.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to a method for detecting the presence of X4 HIV-1 virus in a subject, which virus has selectivity for X4-co-receptors, using the steps described below. The method is performed on sample of a body fluid (which can include, blood serum, plasma, urine, semen, tears, lymph, cerebrospinal fluid, or any other such bodily fluid, or an soluble or partially soluble extract of cells or tissue. The sample may also be cells of tissue from the subject. The subject is one who is known to be infected with the virus. In another embodiment, the method is performed on a sample of a subject suspected of being infected.

The sample must contain nucleic acid and/or protein from which nucleic acid sequences or amino acid sequences are determinable.

The method relies on (a) the amino acid sequence of at least a part of the HIV-1 gp120 V3 region peptide that includes residues 11, 24 and 25 (based on numbering of the V3 loop in the consensus sequence of HIV-1 subtype B beginning with the N-terminal Cys assigned position #1), or (b) from nucleic acid encoding these V3 region peptide.

The method comprises identifying the presence of (i) a positively charged amino acid at any one of positions 11, 24 or 25, or (ii) a codon encoding such positively charged amino acid, or both, wherein the presence of the positively charged amino acid (or its codon in the nucleic acid) is indicative of the presence of the X4 virus in the subject.

Also provided is a method for detecting the presence of R5 HIV-1 virus in a subject, which virus has selectivity for R5-co-receptors, using a method as described above, except that the absence of (i) a positively charged amino acid at any one of positions 11, 24 or 25, or (ii) a codon encoding said positively charged amino acid, or both, is indicative of the presence of the R5 virus in the subject.

A method for detecting the presence of X4 HIV-1 virus in a subject may comprise
(a) in a sample of a body fluid, cells or tissue from a subject infected with (or suspected of being infected with) the virus, determining:
  (i) the nucleic acid sequence of a region that encodes a HIV-1 gp120 V3 loop peptide that includes at least amino acid residues 11, 24 and 25 of V3; or
  (ii) the amino acid sequence of at least a part of the V3 region that includes residues 11, 24 and 25; or
  (iii) both the nucleic acid and amino acid sequence;
(b) identifying the amino acid residue at positions 11, 24 and 25, or the nucleotide sequence encoding said residue, or both, wherein the presence of
  (i) a positively charged amino acid at any one of positions 11, 24 or 25, and/or
  (ii) a codon encoding said positively charged amino acid is indicative of the presence of the X4 virus in said subject, A method for detecting the presence of an R5 HIV-1 virus is performed as above, except that:
  (i) absence of a positively charged amino acid at any one of positions 11, 24 or 25, or
  (ii) absence of a codon encoding the positively charged amino acid is indicative of the presence of the R5 virus in the subject.

The ratio of X4 to R5 virus may also be determined using the above method by determining the ratio of amino acid sequences (or coding nucleotide sequences, or both) in the sample, which have the characteristics of X4 and R5 virus as described above.

The foregoing methods, and information gained therefrom, are useful in screening for small molecule inhibitors of X4 vs R5 viruses, for focusing antiviral therapies based on the predominant or exclusive type of HIV-1 virus present (X4 vs R5) and for creating templates for rational vaccine design.

BRIEF DESCRIPTION OF THE DRAWINGS

FIG. 1A shows optimal local superimposition of β-hairpin 3D structures from $V3_{X4}$ (green), $V3_{R5}$ (red), SDF-1(β2-β3, yellow), MIP-1β(β2-β3, blue). The optimally superimposed local segment that produces this arrangement is indicated within the shaded box. FIG. 1B shows optimal global superimposition of the same 4 β-hairpin structures. For each group the average RMSD for all pairwise comparisons between the four structures is shown in the right column.

FIG. 2A-2D is a group of structural diagrams. The 11 and 25 positions in V3 loops and the homologous positions in the chemokines are in contact with each other and form a single receptor-selective continuous protein surface. Top row of panels is a ribbon depiction of protein backbones with 11 and 25 positions in V3 and the homologous positions in the chemokines displayed as space-filling spheres colored white for carbon, red for oxygen and blue for nitrogen: A) MIP-1β, B) $V3_{R5}$, C) SDF-1 and D) $V3_{X4}$. The portion of the chemokine protein backbone corresponding to the β2-β3 hairpin and containing the 40s loop is colored blue. Middle row of panels shows electrostatic protein surfaces of same view as in the top row of panels. The surface formed by the residues displayed as spheres in top row of panels is circled with a dashed line. -Bottom row of panels: electrostatic surface of all four structures rotated by 90° around the axis drawn between the bottom two rows of panels. In this view the N-loop in the CC-chemokine and its functional equivalent in the CXC chemokine are circled with a solid line while the surface formed by the residues displayed as spheres in top row of panels is circled with a dashe3 line.

DESCRIPTION OF THE PREFERRED EMBODIMENTS

Figure 1A:
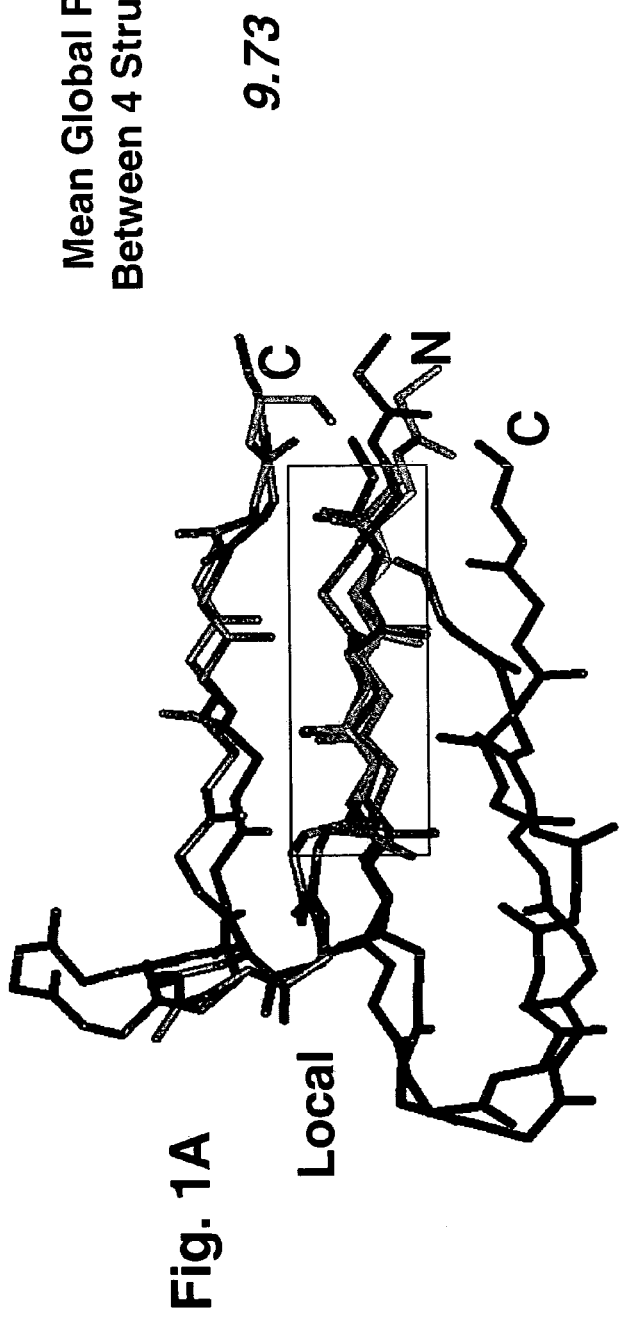
FIGS. 1A-1B show a view of structures.

HIV-1 co-receptor utilization plays a critical role in pathogenesis and disease progression, but the molecular basis of co-receptor specificity is not fully understood. The present inventors discovered that a single positively charged protein surface formed by amino acid residues at the N- and C-terminal edges of the structurally homologous β-hairpins of the V3 loop of the gp120 glycoprotein of X4-type HIV-1 viruses (V3$_{X4}$) and the CXC chemokine SDF-1 targets these molecules to the CXCR4 receptor. Similarly, an equivalent negatively charged or neutral surface on the V3 loop of R5-type HIV-1 viruses (V3$_{R5}$) and on the structurally homologous region of the CC chemokines targets these latter molecules to the CCR5 receptor.

The mechanical details of chemokine receptor selection by HIV-1 and various chemokines are set forth in a model of the structure of this region in the context of activated gp120 (see FIG. 3) and the near 100% accuracy in assigning R5- or X4-tropism to 71 HIV-1 isolates on the basis of the charge of this V3 surface patch (Table 1A/1B). These results provide a structural explanation for the previously derived V3 motifs [13] and sequence constraints [10] used to classify HIV-1 strains into phenotypic categories. The results further support the significance of the homology between the HIV-1 V3 loop and the chemokine β2-β3 hairpin [28], and prove a direct association between this newly identified tropism-determining protein surface and the gp120 bridging sheet.

Table 1A shows an alignment of 42 in vitro confirmed CCR5-exclusive V3 sequences Table 1B shows an alignment of and 29 in vitro confirmed CXCR4-exclusive V3 sequences. Positions 11, 24 and 25 are within the boxes (and their numbers noted along the top of the table. The only sequence that does not conform to the co-receptor selectivity rule described herein is the on named "CMNYU1545". The top line in each alignment shows the consensus sequence of conserved positions: Upper case letter indicates strict conservation of the amino acid. Lower case letter indicates strong conservation of the amino acid residue, + or – indicates conservation of positive or negative. # indicates conservation of a hydrophobic/aromatic residue, % indicates conservation of a small residue (glycine, alanine, serine), The net positive charge for each V3 loop is indicated in parentheses after its name. (All V3 loops have net positive charges).

TABLE 1A

| Position | | 11 | | 24 | 25 | | |
|---|---|---|---|---|---|---|---|
| R5 Consensus | CtRPdNNTR+ | # | #.IGPG.%#YAT | G | d | I IGdIRqA#C | SEQ ID NO:81 |
| D1P95 (7) | CTRPNNNTRK | S | I NIAPGRAFYAT | G | D | I IGDIRQAHC | 10 |
| LP1296 (5) | CTRPNNNTRK | S | I HIQPGRAFYAT | G | E | I IGDIRQAHC | 11 |
| W2P96 (7) | CTRPNNNTRK | S | I HIGPGRAFYAT | G | D | I IGDIRQAHC | 12 |
| W60C (7) | CTRPNNNTRK | S | I HIGPGRAFYTT | G | D | I IGDIRQAHC | 13 |
| W69P (6) | CIRPNNNTRK | S | I HMGPGRAFYAT | G | D | I IGNIRQAHC | 14 |
| CMNYU5487 (5) | CVRPNNNTRK | S | I HIGPGQAFYAT | G | D | I IGNIRQAHC | 15 |
| CMNYU1423 (5) | CTRPNNNTRK | S | I HIGPGQAFYAT | G | D | I IGNIRQAHC | 16 |
| CMNYU360 (6) | CTRPNNNTRK | S | V HIGPGRAFYGI | G | D | I IGNIRQAHC | 17 |
| CMNYU2395 (4) | CTRPNNNTRK | G | V HIGPGRTFYAT | G | E | I IGNIRQAHC | 18 |
| CMNYU809 (6) | CTRPNNNTRK | G | I HIGPGRTFYAT | D | A | I IGNIRQAHC | 19 |
| W64C (6) | CTRPNNNTRK | G | I NMGPGRAFYAT | T | D | I VGDIIQAHC | 20 |
| CMNYU5821 (6) | CTRPNNNTRT | G | V HIGPGRAFYAT | G | D | I IGDIRQAHC | 21 |
| CMNYU6283 (7) | CIRPNNNTRK | S | I RIGPGQAFYAR | G | D | V ISNIRHAYC | 22 |
| CMNYU358 (6) | CIRPNNNTRK | S | I RIGPGQAFYAR | G | D | I IGNIRQAYC | 23 |
| CMNYU1545 (5) | CVRPNNNTRK | S | I HIGPGQALYAT | G | R | I IGDIRRAYC | 24 |
| CMNYU5184 (8) | CIRGNNNTRK | S | M RIGPGQAFYAT | G | D | I IGDIRRAYC | 25 |
| CMNYU4730 (6) | CIRGNNNTRK | S | V RIGPGQTFYTH | G | A | I IGDIRQAHC | 26 |
| CMNYU1989 (6) | CTRPNNNTRR | S | I SIGPGQAFYTT | | D | I IGDIRQAYC | 27 |
| CMNYU2845 (8) | CIRPNNNTRK | S | I PIGPGRAFYAT | G | D | I IGDIRKAYC | 28 |
| CMNYU1500 (7) | CSRPNNNTRK | S | I HIGPGRAFYAT | D | D | I IGNIRQAYC | 29 |
| CMNYU1678 (6) | CTRPGNNTRK | S | I RIGPGQTFYAT | G | D | I IGNIRQAHC | 30 |
| CMNYU5203 (7) | CTRPGNNTRK | S | V RIGPGQTFYAT | G | D | I IGDIRQAHC | 31 |
| CMNYU5285 (6) | CTRPGSNTRK | S | I RIGPGQAFYAT | G | D | V IGDIREASC | 32 |
| CMNYU1532 (3) | CTRPGNNTRK | S | I RIGPGQVLYAT | G | E | I IGEIRQAYC | 33 |
| CMNYU5855 (5) | CTRPGNNTRK | S | V RIGPGQTFYAT | G | D | I IGEIRQAYC | 34 |
| CMNYU4717 (5) | CTRPNNNTRE | S | V RIGPGQTFYAT | G | D | I IGDIRQAHC | 35 |
| CMNYU1261 (5) | CTRPNNNTRR | S | I GIGPGQTIYAT | G | A | I IGDIRQAHC | 36 |
| CMNYU5466 (5) | CTRPSNNTRK | G | W HIGPGQTLYAT | G | A | I IGDIRQAHC | 37 |
| CMNYU5346 (5) | CTRPNNNTRK | S | I RIGPGQALYAT | G | A | I IGNIRQAHC | 38 |
| CMNYU2541 (6) | CTRPNNNTRK | S | I GIGPGQVFYAT | G | D | I IGDIRQAHC | 39 |
| CMNYU786 (5) | CTRPGNNTRK | G | I GIGPGQMFYAT | G | S | I IGDIRQAHC | 40 |
| W67P (7) | CTRPNNNTRR | S | I PMGPGKAFYAT | G | D | I IGDIRQAHC | 41 |
| CMNYU5308 (5) | CTRPSNNTRK | S | I PIGPGQAIYAT | G | E | I IGDIRKAHC | 42 |
| CMNYU5887 (7) | CTRPNNNTRK | S | I HMGPGQAMYVT | G | D | I IGDIRRAHC | 43 |
| tz19 (4) | CTRPNNNTRE | S | I RIGPGQTFYAT | G | D | I IGDIRQAHC | 44 |
| tz14 (5) | CTRPNNNTRK | S | I RIGPGQTFYAT | G | D | I IGDIRQAHC | 45 |
| tz5 (5) | CTRPNNNTRK | S | I RIGPGQVFYAT | G | D | I IGDIRQAHC | 46 |
| tz13 (5) | CIRPNNNTRK | S | V RIGPGQAFYAT | G | D | I IGDIRQAHC | 47 |
| tz9 (5) | CVRPNNNTRK | S | I RIGPGQTFYAT | G | D | I TGDIRQAHC | 48 |
| tz21 (4) | CTRPSNNTRQ | G | I HIGPGQALYTT | | K | I IGDIRQAHC | 49 |
| tz7 (4) | CTRPNNNTRK | S | I HIGPGQAFYAI | G | D | V IGNIRQAQC | 50 |
| tz11 (4) | CIRPNNNTRK | S | VHIGPGQTFYAT | G | D | I IGNIRQAHC | 51 |

R5 consensus is the consensus sequence of conserved positions:

Upper case letter: strict conservation of the amino acid.

Lower case letter: strong conservation of the amino acid residue.

+ or – indicates conservation of positive or negative residue.

# indicates conservation of a hydrophobic/aromatic residue, "%" indicates conservation of a small residue (Gly, Ala, Ser), The net positive charge for each V3 loop is indicated in parentheses after its name. (All V3 loops have net positive charges).

TABLE 1B

| Position | | 11 | | 24 | 25 | | |
|---|---|---|---|---|---|---|---|
| X4 Cons | CTRPNNNtR. | * | R I.#GPGRA#Y.T | G | | I #..GdI+.A#C | SEQ ID NO:82 |
| DY1C (6) | CTRPNNNTR- | K | R IHIGPGRAFYTT | G | Q | I I--GNIRQAYC | 52 |
| 71_1C1 (6) | CTRPNNNTR- | K | R IHIGPGRAFYTT | G | Q | I I--GNIRQAHC | 53 |
| 72_C9 (7) | CTRPNNNTR- | K | R IHIGPGRAFHTT | G | A | I I--GKIRQAHC | 54 |
| RRmtc_ (6) | CTRPNNNTR- | K | R IHIGPGRAFYTT | G | G | I I--GNIRQAHC | 55 |
| DY11P_ (8) | CTRPNNNTR- | K | R IHIGPGRAFYAT | G | K | I I--GDIRQAHC | 56 |
| 12P49_ (7) | CIRPNNNTR- | R | R IHIGPGRAFYAT | G | R | I I--GNIRQAYC | 57 |
| W12P04 (8) | CIRPNNNTR- | R | S IHIGPGRAFYAT | G | R | I I--GDIRRAYC | 58 |
| AF2P12 (6) | CIRPNNNTR- | T | K IRIGPGQAFYAT | G | N | I I--GDIRQAYC | 59 |
| DY9P_7 (6) | CLRPNNNTR- | K | R IHLGPGRAFYAA | G | E | I I--GKIRQAHC | 60 |
| P1T6C (9) | CTRPNNNIR- | R | R IHIGPGRAFYAT | G | D | I I--GDIRKAYC | 61 |
| P1T36C (9) | CTRPNNNTR- | R | R IHIGPGRAFYAT | G | D | T I--GDIRKAYC | 62 |
| AF10P9 (9) | CTRPNDNIR- | K | R VHIGPGQAFYAT | G | D | V I--GDIRRAHC | 63 |
| P14T0C (9) | CTRPNNNIR- | R | R IHIGPGRAFYAT | G | G | I R--GDIRKAYC | 64 |
| Acmtc (9) | CTRPNNNIR- | R | R IRIGPGRAYFTR | G | Q | I K--EHMRKAHC | 65 |
| CMmtc (10) | CTRPSNNTR- | K | R IPIGPRRAFYAT | G | D | I V--GDIRRAHC | 66 |
| P5T0C (7) | CTRPNNHTR- | K | R MTLGPGRVYYTT | G | E | I L--GDIKKAHC | 67 |
| P5T6C (7) | CTRPNNHTR- | K | R MTLGPGKVYYTT | G | E | I V--GDIKKAHC | 68 |
| XP6_6 (6) | CTRPNNHTR- | K | R ISLGPGRAYYTT | G | E | I V--GSIKKAHC | 69 |
| P4_14 (9) | CTRPNNNTR- | K | R IRIGPGRAVYTT | G | K | I I--GKIRQAHC | 70 |
| FR3_4 (9) | CTRPNTNKR- | K | R TTKGPGRVIYAT | G | Q | I I--GKIRQAHC | 71 |
| VE15_2 (6) | CTRPNNNTR- | K | R ISIGPGRAFYTT | G | Q | I I--GNIRQAHC | 72 |
| DE2_4 (6) | CTRPNNNTR- | K | R ISIGPGRAFYTI | G | Q | I I--GNIRQAHC | 73 |
| W17P07(6) | CTRPNNNTR- | K | G ISVGPGRAIYAT | K | N | I I--GDISQAHC | 74 |
| W2P069 (6) | CTRPKNNTR- | K | P IHIGPGRAFYAT | R | E | I R--GNIIQAHC | 75 |
| 17P7_9 (6) | CTRPNNNTR- | K | R ISVGPGRAFYAT | G | N | I I--GKISQAHC | 76 |
| EV5_2 (8) | CTRPNNNTR- | K | R IRIGPGRAFYTT | G | Q | I I--GDIRQAHC | 77 |
| AF9P2 (4) | CTRPNNNTI- | T | R IRIGPGQAFYAT | G | S | I I--GNIRQAHC | 78 |
| tz23 (8) | CSRPYKKER- | Q | R THIGPGQALYTT | R | T | T RVEGNIRQAHC | 79 |
| tz24 (7) | CVRPYRNIKI | Q | R TPIGLGQALYTT | K | R | I ---GHIGQAHC | 80 |

The numbering of positions in the V3 loop region of gp120, as used herein, is based on the numbering of the V3 loop in the consensus sequence of HIV-1 subtype B, and begins with the N-terminal Cys being assigned position 1.

The present inventors generated 3D structural models of 71 receptor-restricted V3 loops as peptides and in the context of the whole activated gp120 molecule. The collection of models has allowed the inventors to identify the surface on these models which is associated with chemokine receptor selectivity and which defines, or dominantly contributes to, co-receptor tropism. The character of the protein surface identified herein may be approximated by a highly predictive sequence "rule" or "algorithm" that serves as the basis of the present methods. The rule states that:

If a positively charged amino acid is present at any of positions "11", "24" or "25", an X4 virus is present; otherwise an R5 virus is present.

In another embodiment, the 3D shape and electrostatic character of these surfaces also directly serve as templates for rational design of small molecule inhibitors of these virus-receptor interactions, permitting the design of a new class of anti-HIV drugs.

In another embodiment, the atomic level of detail for the exact protein interfaces between gp120 and its chemokine co-receptors provides a means to identify epitopes that may guide rational vaccine design.

The virus sample (e.g., plasma) that is used in the present methods is preferably extracted to obtain total RNA, cDNA, or if cells are the sample, then DNA is extracted. Appropriate primers are used in PCR reaction to obtain the V3 sequence. Typically, such primers fall outside the V3 region on either side. The length of viral sequence for analysis may comprise the entire V3 loop (25 amino acids or 75 nucleotides) and may be as few as 10 amino acid residues. Thus, a given sequence can be screened to determine, according to the above rule, whether the sample is exclusively X4 or R5 viruses, or whether both types co-exist in the sample.

In another embodiment, rather than isolating and sequencing the nucleic acid, total nucleic acid can be tested for hybridization with overlapping oligonucleotides which are arrayed on a chip or other solid support. This method is a proxy for sequencing since the sequences of the oligos are known. Such technology is well-known in the art (Affymetrix chips, production information available on line, etc. as well as other known technologies in the art).

Mass spectrometry can also be used on peptide fragments to obtain sequence information.

Interestingly, a parallel exists in an unrelated protein that binds to CCR5: the cyclophilin of *Toxoplasma gondii*. The only two mutation that abolish this protein's binding to CCR5 follows the same structural theme described herein for V3 and the chemokines. The mutated residues are located in contact with each other at the extreme N- and C-termini of two anti-parallel β-strands that are homologous to the β-hairpins described here [52].

The fact that regions other than the presently described surface of the V3 loop in gp120 and the β2-β3 hairpin of the chemokines have been implicated in receptor binding [1, 47, 51, 53-56), are not inconsistent with the present invention. Crystallographic and NMR findings show that the edge of the N-terminal strand of the V3 loop makes the predominant contact with broadly neutralizing anti-V3 mAb 447, suggesting that this N-terminal β-strand surface binds to the chemokine receptor. Although it is not possible to rule out the possibility that the V3 loop N-terminal N-strand binds to the chemokine receptor, the present invention suggest a more likely explanation—that the basis of virus neutralization by mAb 447 is non-competitive. Thus, in the context of the emerging "fuller" gp120 model as described herein, binding of a mAb to the N-terminal strand (black arrow in FIG. 3) would force the V3 loop to move along the red curved arrow shown in FIG. 3, burying the indicated (circled) "11/25" surface patch, sterically hindering docking of the chemokine receptor and preventing the critical gp120/co-receptor interaction. Recent data allowed resolution of the 3D crystallographic structure of the gp120 core containing the complete V3 loop [57]. The position of the V3 loop in this structure relative to the bridging sheet is similar to that shown for the β2-β3 hairpin in the present model shown in FIG. 3, where the homologous "11/25" patch appears to be contiguous with the bridging sheet, while the tip of the V3 loop points away from this surface. Moreover, the present model is supported by considerable experimental data indicating a close physical and functional interaction between the bridging sheet and the V3 loop [1, 53-56].

Figure 3:
FIG. 3 is a model of a gp120 construct with the chemokine SDF-1 replacing the chemokine homologous portion of the V3 loop. The gp120 core is shown in grey ribbon. CD4 is shown in blue ribbon. mAb17b, a bridging sheet binding antibody, is shown in green ribbon and approximates the location of the chemokine receptor bound to gp120. The SDF-1 molecule, tethered to the V3 stem, was optimally docked to the surface of this complex (see Examples for Methods). $V3_{MN}$, superimposed on the homologous β2-β3 hairpin of MIP1β, is shown in red. The black arrow indicates the location along the edge of $V3_{MN}$ where the neutralizing 447 mAb is bound based on the study of Stanfield et al., 2004 [29]. The red curved arrow indicates the rotation of the $V3_{MN}$ hairpin that would be required in order to accommodate binding of mAb 447 to $V3_{MN}$ without steric hindrance from gp120, i.e., $V3_{MN}$ would have to oppose its C-terminal β-strand to gp120 in order to expose its N-terminal strand to open solution for binding of mAb 447 in the model depicted. A neutralized position with mAb 447 bound would place the tip of the V3 hairpin in the space occupied by the mAb17b/chemokine receptor, and the 11/25 surface buried against gp120, as identified by the present inventors and disclosed herein. In the absence of the antibody, the V3 would be free to assume an active position with the 11/25 surface (circled) pointing towards mAb17b and the tip away from the chemokine receptor, as shown.

The positively-charged β-turn at the tip of the V3 loop has also been implicated in chemokine receptor binding. This area may interact with cell surface glycosaminoglycans (GAG) [58-60] as well as with the long and highly mobile N-terminal region of the chemokine receptors which bears a strong negative charge due in part to the presence of sulfated tyrosines [2, 61]. In the chemokines, the 40s loop (which forms the central section of the β2-β3 hairpin) is also implicated in GAG binding [47, 51]. The β-turn at the tip of the V3 loop and the homologous β-turn in the 40s loop of the chemokine β2-β3 hairpin appear to play an important role in targeting the virus and the chemokines to the cell surface, but may play a lesser or indirect role in binding to the chemokine receptor. This is consistent with the positioning of the tip of the V3 loop and the 40s loop as shown in FIG. 3, which points away from the bridging sheet and the core of gp120 and may be located in approximately the region where one would find proteoglycan "branches" lining the cell membrane surface.

In contrast, the mid-region of the C-terminal half of the V3 loop that interacts with the second extracellular loop (ECL-2 loop) of the CXCR4 [1]. Interestingly, the ECL-2 loop carries a net positive charge in CCR5 and a net negative charge in CXCR4 [46, 62], an arrangement that is complementary to the charge of the key surfaces identified herein in R5 and X4-tropic viruses. Thus, a "unified model" combining the present observations with the findings of others supports the present invention's new model for gp120 (and chemokine) binding to chemokine receptors which involves one or more non-selective sites as well as a co-receptor selective site. The non-selective site would include the β-turn at the tip of the V3 loop (and the chemokine 40s loop) and as well as the N-loop and the bridging sheet in the gp120 (and chemokines) respectively.

The selective site is the surface identified herein. Indeed, according to the present invention, as supported by studies by others (e.g., A. Trkola et al., Nature, 1996, 384:184-7; C M Hill et al., J Virol., 1997, 71:6296-6304; N G Hoffman et al., J Virol., 2002, 76:3852-64; C. Blanpain et al., J Biol Chem, 2003, 278:5179-87) a two-site models for gp120 and chemokine binding to chemokine receptors explains the observations.

As described herein, the N-loop of the CC-chemokines is adjacent to the "11/25 patch" (FIGS. 2A and 2C) and that, while the functional equivalent of the N-loop of the chemokine SDF-1 is located further proximally toward the N-terminus (residues 8-12), it is also adjacent to the "11/25 patch". According to the present invention, the bridging sheet of gp120 is similarly adjacent to the 11/25 patch (FIG. 3).

The critical receptor binding residues described earlier in CC and CXC chemokines tend to be electropositive. Similarly, prior studies of the gp120 bridging sheet showed a requirement for this sheet for interaction with both types of chemokine receptors, and that positive charges played a role in its influence [54, 55]. According to the present invention, the N-loop of the CC chemokines and its equivalent in SDF-1 is a critical, though non-selective, region involved in receptor binding, probably analogous to the bridging sheet of gp120.

According to the present invention, a dual-tropic HIV-1 strain (for CCR5 and CXCR4) must be able to easily adopt two different conformations in order to switch between the two types of "11/25" surfaces described herein. The disordered state of the V3 loop may confer this property on some V3 sequences, although the limits of structural adaptability, along with studies of true dual-tropic HIV-1 strains, suggest that such sequences are rare [75].

The ability to reliably predict HIV-1 co-receptor usage based upon the sequence of the V3 loop serves as the basis of a number of important utilities of the present invention. In addition to earlier detection of the presence of X4-tropic viruses in a subject, which has implications for clinical disease management, as discussed herein, the present invention serves as a basis for advancing HIV-1 drug discovery and vaccine design.

HIV-1 strains that are transmitted in vivo generally use the R5 co-receptor, while X4 strains, in contrast, usually emerge after years of infection and herald clinical and immunologic decline.

The understanding of the 3D structure of the V3 loop as disclosed herein (and of the β2-β3 hairpin of the chemokines) simplifies the determination of HIV-1 co-receptor usage in infected individuals. Determination of HIV-1 co-receptor usage in a patient helps to individualize antiretroviral treatment by identifying, or changing the time to initiate, therapeutic approaches and the choice of therapeutic agents that are best suited to a specific individual and his/her particular viral burden. In addition, this determination helps identify targets for antiretroviral therapy.

Having now generally described the invention, the same will be more readily understood through reference to the following examples which are provided by way of illustration, and are not intended to be limiting of the present invention, unless specified.

EXAMPLE I

Experimental Procedures and Materials

1. Pairwise Local and Global Superimposition

Global superimpositions were performed by minimization of root-mean-square-deviation (RMSD) of each rigid body pair of β-hairpins [63-66]. Local superimpositions were performed by a modified method of differences between interatomic distances as implemented in the ICM software suite [67, 68]. Each method results in an RMSD score and, as shown in Table 2 The former corresponds to superimposing the whole structure in every pairwise comparison, while the latter corresponds to superimposing only the N-terminal strands between pairs of structures in some of the comparisons. The sequence alignment from each valid pairwise global alignment was then extracted and concatenated into the equivalent of a single multiple sequence alignment, more accurately termed a "structure-based residue equivalency table," shown in Table 1A/1B.

2. Protein Structural Modeling

All modeling manipulations and graphical analysis and production were performed in the ICM software environment which utilizes an internal coordinate tree description and fast algorithms approximating the solvation energy of proteins in solution [67, 69]. The structures of $V3_{X4}$ and $V3_{R5}$ were extended to position 26 at each C-terminus using the homologous structures of SDF-1 and MIP-1β respectively as templates. Positions 24, 25 and 26 and contacting side-chains were then predicted in an ab initio simulation protocol that has been shown to be capable of accurately predicting the structure of short peptide segments [69]. The same protocol was used to predict the conformation of each V3 loop in the context of gp120 with the β-hairpin fixed as a rigid body and the stem segments (residues 2-10 and 27-end of the V3) free to change conformation in the modeling. A similar energy minimization protocol for the docking of two rigid proteins was used to build the model of SDF-1 in the context of gp120 (FIG. 3)[70]. Coordinates of all structural models will be deposited in the public Protein Data Bank upon publication of the results.

3. Sequence Alignments

The full set of V3 sequences were aligned using global alignment methods [71] with structurally tuned parameters [72].

4. X4 and R5 Sequences

To avoid ambiguity and to reduce selection bias, a set of 71 HIV-1 isolates was employed, each of whose co-receptor usage had been unambiguously described in the literature [77, 78] or using a clonotypic assay. Thus, all sequences analyzed herein were derived from early passaged primary isolates or from biologic or molecular clones, were found to use exclusively CXCR4 or CCR5 in vitro, and none had ever been passaged in cell lines.

Biological and molecular clones were isolated from HIV-1-infected patients from New York, New Jersey, and Kenya [73-75]. The institutional review boards at each clinical site and the New York State Department of Health approved the investigation, and each individual provided informed consent at enrollment. Primary isolates of HIV-1 were obtained by co-culture of the peripheral blood mononuclear cells (PBMCs) from HIV-1 infected individuals with PBMCs from normal donors; biological clones were then derived from primary isolates by short-term limiting dilution cloning. The co-receptor phenotype of each biological clone was determined by using a HOS-CD4 assay [75]. Alternatively, full-length env genes were molecularly cloned directly from plasma-derived HIV-1 RNA by using reverse transcription and long PCR amplification, under limiting dilution reaction conditions. Functional phenotypic analyses of gp160 env clones by employing a cell fusion assay described previously [76]. Of >1200 env genes obtained from individuals exhibiting a broad spectrum of HIV-1 subtypes and disease states and tested in phenotypic assays at the Wadsworth Center (Albany, N.Y.), none was dual tropic, and all were found to use either the R5 or X4 co-receptor [75].

Receptor usage of primary isolates reported in the literature was based on growth of PBMC-derived viruses in engineered cell lines expressing CD4 and either CXCR4 or CCR5 [77, 78]. A total of 71 isolates were used in the analysis. Selection bias was minimized by using directly-tested two sets of primary isolates from the literature and a third set composed of biologic and molecular clones, by including all sequences from the three data sets, i.e., no data were excluded, by using only one sequence per patient at any one time point, and by including data from viruses derived from clades A, AG, B, D, F, G and H.

EXAMPLE II

Structural Basis of the 11/25 Rule

Figure 1B:
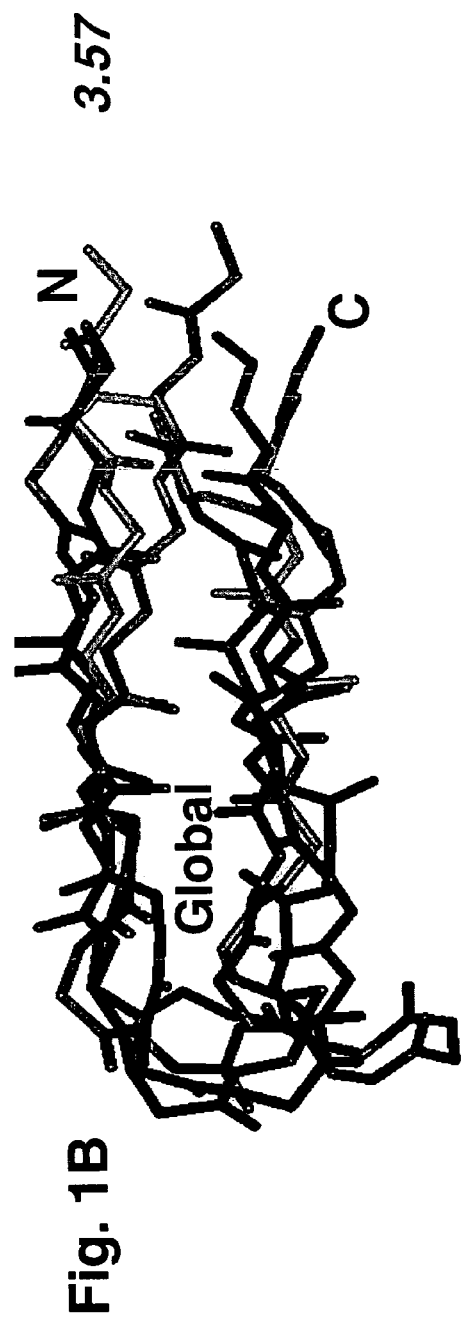

To investigate the structural basis of the 11/25 rule, the 3D organization of the following structures was compared atom-by-atom. All of these bind to the receptors for either CC or CXC chemokines: the β2-β3 hairpins of the CC chemokines RANTES, MIP-1α, and MIP-1β, the β2-β3 hairpin of the CXC chemokine SDF-1, and the β-hairpin structures assumed by the V3 peptides from HIV-1 strains IIIB and MN complexed with neutralizing mAbs 0.5β and 447-52D, respectively [27-29, 48, 49]. Optimal superimposition of two protein structures is frequently ambiguous [50]. Usually the choice is between the best local and the best global superimposition (see Methods), and this was the case in this study. The optimal local superimposition which superimposes the 3 or 4 residue segment of the structures with the best RMSD, a quantitative measure of the aggregate distances between atoms of two 3D structures, was previously shown in [28] and was found between the N-terminal β-strands of four structures (MIP-1β, SDF-1, $V3_{R5}$ and $V3_{X4}$), but this orientation results in a 180° divergence of two of the C-terminal β-strands (FIG. 1A). Global superimposition, which finds the minimal RMSD between the whole set of sequence-aligned Cα atoms of the compared β-hairpins, results in the comparison shown in FIG. 1B in which each of the β-hairpins occupies a similar envelope in space. The global superimposition orientation was selected as the basis for this study because it minimized the RMSD The global superposition allowed construction of a 3D structure-based, residue-to-residue equivalency (pairwise structural alignment) between all of the experimentally resolved V3 and chemokine β-hairpin structures (Table 2. These relationships were integrated into a single, maximally accurate, structure-based, multiple alignment, and the positions corresponding to or homologous to the "11" and "25" positions were precisely identified in all the proteins. Any V3 sequence may be reliably aligned by standard methods to this table, and a structural model built by homology. The critical C-terminal residue at V3 position "25" that helps determine tropism is not present in the V3 structures solved to date, but the residue equivalency table created here and the underlying homology between the V3 β-hairpin and the chemokine β2-β3 hairpins, allowed the modeling of its 3D structure. As shown in Table 2 homology modeling aligned the "25" V3 position with K54 in SDF-1, E54 in RANTES, and S55 in MIP-1β and MIP-1α. The functional consequences of mutation of this position in the chemokines has not been reported.

In the present V3 models, the residue at V3 position "25" is in contact in 3D space with the residue at V3 position "11" in the N-terminal β-strand of the $V3_{R5}$ and $V3_{X4}$ hairpins and forms a single continuous protein surface (FIGS. 2A and 2B, top row). This protein surface patch is electropositive in the $V3_{X4}$ loops and electronegative in the $V3_{R5}$ loops (FIGS. 2B and 2D, bottom two rows). Thus, the two tropism-determining residues in V3, although separated by 13 residues in the primary sequence, contact each other in 3D space and form a single continuous surface (the "11/25 patch") with opposite charges in the X4 and R5 V3 loops.

Furthermore, the protein surface that is homologous by sequence to this V3 11/25 surface in the chemokines is electropositive in SDF-1 and electronegative in MIP-1β (FIGS. 2A and 2C,). Interestingly, the positively charged N-loop surface in MIP-1β (amino acids 12-25), a structure known to be critical for receptor binding, lies directly next to the residues of the key protein surface identified here.

TABLE 2

| Source | Sequence 11 25 | SEQ ID NO: |
|---|---|---|
| V3_JRCSF | ----------------------------CTRPSNNTRK$\underline{S}$IHIGP---GRAFYTT-G$\underline{E}$IIGDIRQAHC------ | 2 |
| V3_SF162 | ----------------------------CTRPNNNTRK$\underline{S}$ITIGP---GRAFYAT-G$\underline{D}$IIGDIRQAHC------ | 3 |
| V3_MN/447 | ---------------------------------------K$\underline{R}$IHIGP---GRAFYTT------------------ | 4 |
| V3_IIIB/0.5b | ---------------------------------------RK$\underline{S}$IRIQR-GPGRAFVTI------------------ | 5 |
| SDF-1 | ------SYRCPCRFFESHVARANVKHLKILNTPNCA-LQ$\underline{I}$VARLKN--NNRQVCIDP$\underline{K}$LKWIQEYL-EKALN-- | 6 |
| RANTES | --GYSSDTTPCCFAYIARPMPRAHIKEYFYTSGKCSNPA$\underline{\underline{V}}$VFVTR---KNRQVCANP$\underline{E}$KKWVREYI-N-SLEMS | 7 |
| MIP1-β | APMGSDPPTACCASYTARKLPRNFVVDYYETSSLCSQPA$\underline{\underline{V}}$VFQTK---RSKQVCADP$\underline{S}$ESWVQEYVYDLELN-- | 8 |
| MIP1-α | -SLAADTPTACCFSYTSRQIPQNFIAAYFETSSQCSKPG$\underline{\underline{V}}$IFLTK---RSRQVCADP$\underline{S}$EEWVQKYVSDLELSA- | 9 |

Table 2 provides an amino acid residue equivalency table (structure based sequence alignment) between five homologous β-hairpins among known V3 and chemokine structures (names of these five known structures are displayed in bold letters). Sequence alignment of two V3 sequences without known structure to the known structures (names of these two sequences are in plain, non-bolded letters). The positions corresponding to the 11 and 25 positions are displayed as underscored letters:negatively charged amino acids, italicized for positively charged amino acids and double underscored for hydrophobic amino acids. With knowledge of the tropism of any V3 region, the 3D structure of the loop may be modeled by homology through alignment of the V3 sequence to this table.

EXAMPLE III

Determination of Location and Orientation of Surface: Residues 11, 24 and 25

To determine the location and orientation of this surface in its full biological context, an energy minimized model was built of SDF-1 fused to the stem of V3 on the full crystallographic structure of gp120 [37, 38], a construct that is known to be infective [20]. The model shows that SDF-1 can only fit without clashing in one orientation (FIG. 3). This orientation finds the 11/25 patch identified here in contact with the gp120 bridging sheet and facing the space presumably occupied by the chemokine receptor (which, in the crystal structure, is occupied by mAb 17b). mAb 17b recognizes an epitope in the bridging sheet of gp120 involved in binding to the chemokine receptor. Interestingly, this model places the β-turn at the tip of the β2-β3 hairpin (the 40s loop) on the opposite side of the molecule at a distance that is 25 Å away from the presumed chemokine receptor location on gp120 [51]. These data together suggest that the 11/25 patch formed by residues at the base of the β-strands in the homologous V3 loop and β2-β3 chemokine hairpin is the surface responsible for chemokine receptor selection by both gp120 and the chemokines.

According to the present analysis, the nature of the charge at this surface appears to play the critical discriminating role in receptor selection. Close inspection of the homology models near the "25" position suggests that this position in both the chemokines and the V3 loop is characterized by a local random coil backbone structure (not an α-helix nor a β-strand) and that, in the V3 loop, the side chain at position 25 actually occupies the region of space normally occupied by the side chain of the residue at position 24 whenever a glycine residue (which has no side chain) is present at position 24.

To investigate this observation further, the sequences from 29 isolates that were shown experimentally to use exclusively CXCR4 and the sequences from an additional 42 isolates that exclusively used CCR5 were examined these 71 viruses represented HIV-1 subtypes A, AG, B, D, F, G and H (Table 1A and 1B). With these sequences, the present inventors produced 3D models of each based on the present structure-based alignment table. In every case, charged residues that appeared at positions 24 and 25 were found to contribute to the 11/25 patch. When glycine was present at position 24, which is the most common case, the side chain of residue 25 forms approximately the same protein surface as does a non-glycine side chain at position 24. This is likely related to the fact that glycine is the amino acid with the smallest volume and most flexible backbone and that, therefore, Gly-Xaa may potentially occupy the same overall volume and orientation on a random coil backbone as a single bulky residue Xaa. Thus, the critical surface patch identified here for the first time in the 71 V3 3D models is formed by residues 11, 24 and 25 within the sequence of each V3 loop.

EXAMPLE IV

Testing Biological Relevance

To assess the biologic relevance of the present models of the V3 loop and of this surface vis-à-vis usage of the CXCR4 and CCR5 chemokine receptors, the present inventors again used this experimentally-defined set of HIV-1 V3 sequences (Table 1A/1B). In every one of the models based upon the V3 sequences of 29 X4-exclusive isolates, a positively charged residue occupied position 11, 24 or 25, forming an electropositive patch. In contrast, only two positively charged residues were found in any of these three positions in the sequences of the 42 R5 isolates studied. It is noteworthy that these specific charges do not correlate with the net charge in the whole V3 loop. (See Table 1A/1B).

Further analysis revealed that for 39 R5 sequences, there is an observable partial (δ) net negative charge at the relevant surface patch (not shown). Thus, the modeling of the V3 regions of 71 HIV-1 isolates suggests a sequence rule that can approximate the determinants of this critical protein surface and predicts with 95.2% accuracy ($\chi^2 \approx 0.001$), the receptor tropism of the isolates. The rule is as follows:

If a positively charged amino acid is present at any of positions "11", "24" or "25", an X4 virus is present; otherwise an R5 virus is present.

Thus, in the present set which consists of isolates from HIV-1 subtypes (clades) A, AG, B, D, F, G, and H, the presence of one (or more) positively charged residues in these three positions of V3 predicts X4 tropism with 100% sensitivity and 95.2% specificity. Conversely, the absence of a positively charged residue from these positions predicts R5 tropism with 95.2% sensitivity and 100% specificity.

REFERENCES CITED

1. Labrosse, B., Treboute, C., Brelot, A. & Alizon, M. (2001) *J Virol* 75, 5457-64.
2. Cormier, E. G. & Dragic, T. (2002) *J Virol* 76, 8953-7.
3. Fouchier, R. A., Groenink, M., Kootstra, N. A., Tersmette, M., Huisman, H. G., Miedema, F. & Schuitemaker, H. (1992) *J Virol* 66, 3183-7.
4. Cordonnier, A., Montagnier, L. & Emerman, M. (1989) *Nature* 340, 571-4.
5. Chesebro, B., Wehrly, K., Nishio, J. & Perryman, S. (1992) *J Virol* 66, 6547-54.
6. De Jong, J., Simon, F., Van der Groen, G., Baan, E., Saragosti, S., Brun-Vezinet, F. & Goudsmit, J. (1996) *AIDS Res Hum Retroviruses* 12, 1503-7.
7. Harrowe, G. & Cheng-Mayer, C. (1995) *Virology* 210, 490-4.
8. Hwang, S. S., Boyle, T. J., Lyerly, H. K. & Cullen, B. R. (1991) *Science* 253, 71-4.
9. Kato, K., Sato, H. & Takebe, Y. (1999) *J Virol* 73, 5520-6.
10. De Jong, J. J., De Ronde, A., Keulen, W., Tersmette, M. & Goudsmit, J. (1992) *J Virol* 66, 6777-80.
11. Shioda, T., Levy, J. A. & Cheng-Mayer, C. (1991) *Nature* 349, 167-9.
12. Shioda, T., Levy, J. A. & Cheng-Mayer, C. (1992) *Proc Natl Acad Sci USA* 89, 9434-8.
13. Xiao, L., Owen, S. M., Goldman, I., Lal, A. A., deJong, J. J., Goudsmit, J. & Lal, R. B. (1998) *Virology* 240, 83-92.
14. Verrier, F., Burda, S., Belshe, R., Duliege, A.-M., Excler, J.-L., Klein, M. & Zolla-Pazner, S. (1999) in *Molecular Approaches to Vaccine Design*, ed. Laboratory, CSH, Cold Springs Harbor, N.Y.).
15. Blaak, H., van't Wout, A. B., Brouwer, M., Hooibrink, B., Hovenkamp, E. & Schuitemaker, H. (2000) *Proc Natl Acad Sci USA* 97, 1269-74.
16. Berger, E. A., Doms, R. W., Fenyo, E. M., Korber, B. T., Littman, D. R., Moore, J. P., Sattentau, Q. J., Schuitemaker, H., Sodroski, J. & Weiss, R. A. (1998) *Nature* 391, 240.
17. Chiou, S. H., Freed, E. O., Panganiban, A. T. & Kenealy, W. R. (1992) *AIDS Res Hum Retroviruses* 8, 1611-8.
18. Cao, J., Sullivan, N., Desjardin, E., Parolin, C., Robinson, J., Wyatt, R. & Sodroski, J. (1997) *J Virol* 71, 9808-12.
19. Yang, Z. Y., Chakrabarti, B. K., Xu, L., Welcher, B., Kong, W. P., Leung, K., Panet, A., Mascola, J. R. & Nabel, G. J. (2004) *J Virol* 78, 4029-36.
20. Yonezawa, A., Hori, T., Takaori-Kondo, A., Morita, R. & Uchiyama, T. (2001) *J Virol* 75, 4258-67.
21. Conley, A. J., Gorny, M. K., Kessler, J. A., 2nd, Boots, L. J., Ossorio-Castro, M., Koenig, S., Lineberger, D. W., Emini, E. A., Williams, C. & Zolla-Pazner, S. (1994) *J Virol* 68, 6994-7000.
22. Gorny, M. K., VanCott, T. C., Hioe, C., Israel, Z. R., Michael, N. L., Conley, A. J., Williams, C., Kessler, J. A., 2nd, Chigurupati, P., Burda, S. & Zolla-Pazner, S. (1997) *J Immunol* 159, 5114-22.
23. Gorny, M. K., Revesz, K., Williams, C., Volsky, B., Louder, M. K., Anyangwe, C. A., Krachmarov, C. P., Kayman, S. C., Pinter, A., Nadas, A., Nyambi, P. N., Mascola, J. R. & Zolla-Pazner, S. (2004) *J Virol* 78, 2394-2404.
24. Gorny, M. K., VanCott, T. C., Williams, C., Revesz, K. & Zolla-Pazner, S. (2000) *Virology* 267, 220-228.
25. Zolla-Pazner, S. (2004) unpublished data.
26. Ding, J., Smith, A. D., Geisler, S. C., Ma, X., Arnold, G. F. & Arnold, E. (2002) *Structure (Camb)* 10, 999-1011.
27. Tugarinov, V., Zvi, A., Levy, R., Hayek, Y., Matsushita, S. & Anglister, J. (2000) *Structure Fold Des* 8, 385-95.
28. Sharon, M., Kessler, N., Levy, R., Zolla-Pazner, S., Gorlach, M. & Anglister, J. (2003) *Structure (Camb)* 11, 225-36.
29. Stanfield, R. L., Gorny, M. K., Williams, C., Zolla-Pamer, S. & Wilson, I. A. (2004) *Structure* 12, 193-204.
30. Weliky, D. P., Bennett, A. E., Zvi, A., Anglister, J., Steinbach, P. J. & Tycko, R. (1999) *Nat Struct Biol* 6, 141-5.
31. Rini, J. M., Stanfield, R. L., Stura, E. A., Salinas, P. A., Profy, A. T. & Wilson, I. A. (1993) *Proc Natl Acad Sci* 90, 6325-9.
32. Stanfield, R., Cabezas, E., Satterthwait, A., Stura, E., Profy, A. & Wilson, I. (1999) *Structure Fold Des* 7, 131-42.
33. Ghiara, J. B., Stura, E. A., Stanfield, R. L., Profy, A. T. & Wilson, I. A. (1994) *Science* 264, 82-5.
34. Milich, L., Margolin, B. & Swanstrom, R. (1993) *J Virol* 67, 5623-34.
35. Resch, W., Hoffman, N. & Swanstrom, R. (2001) *Virology* 288, 51-62.
36. Briggs, D. R., Tuttle, D. L., Sleasman, J. W. & Goodenow, M. M. (2000) *Aids* 14, 2937-9.
37. Kwong, P. D., Wyatt, R., Majeed, S., Robinson, J., Sweet, R. W., Sodroski, J. & Hendrickson, W. A. (2000) *Structure Fold Des* 8, 1329-39.
38. Kwong, P. D., Wyatt, R., Robinson, J., Sweet, R. W., Sodroski, J. & Hendrickson, W. A. (1998) *Nature* 393, 648-59.
39. Dyson, H. J. & Wright, P. E. (2002) *Curr Opin Struct Biol* 12, 54-60.
40. Dunker, A. K., Garner, E., Guilliot, S., Romero, P., Albrecht, K., Hart, J., Obradovic, Z., Kissinger, C. & Villafranca, J. E. (1998) *Pac Symp Biocomput*, 473-84.
41. Zvi, A., Tugarinov, V., Faiman, G. A., Horovitz, A. & Anglister, J. (2000) *Eur J Biochem* 267, 767-79.
42. Zvi, A., Kustanovich, I., Hayek, Y., Matsushita, S. & Anglister, J. (1995) *FEBS Lett* 368, 267-70.
43. Zvi, A., Feigelson, D. J., Hayek, Y. & Anglister, J. (1997) *Biochemistry* 36, 8619-27.
44. Tugarinov, V., Zvi, A., Levy, R. & Anglister, J. (1999) *Nat Struct Biol* 6, 331-5.
45. Kuiken, C., Foley, B., Freed, E., Hahn, B., Marx, P., McCutchan, F., Mellors, J. W. & Wolinsky, S. (2002) *HIV Sequence Compendium* 2002 (Theoretical Biology and Biophysics, Los Alamos).
46. Rojo, D., Suetomi, K. & Navarro, J. (1999) *Biol Res* 32, 263-72.
47. Bondue, A., Jao, S. C., Blanpain, C., Parmentier, M. & LiWang, P. J. (2002) *Biochemistry* 41, 13548-55.
48. Lodi, P. J., Garrett, D. S., Kuszewski, J., Tsang, M. L., Weatherbee, J. A., Leonard, W. J., Gronenborn, A. M. & Clore, G. M. (1994) *Science* 263, 1762-7.
49. Crump, M. P., Gong, J. H., Loetscher, P., Rajarathnam, K., Amara, A., Arenzana-Seisdedos, F., Virelizier, J. L., Baggiolini, M., Sykes, B. D. & Clark-Lewis, I. (1997) *Embo J* 16, 6996-7007.
50. Feng, Z. K. & Sippl, M. J. (1996) *Fold Des* 1, 123-32.

51. Laurence, J. S., Blanpain, C., De Leener, A., Parmentier, M. & LiWang, P. J. (2001) *Biochemistry* 40, 4990-9.
52. Yarovinsky, F., Andersen, J. F., King, L. R., Caspar, P., Aliberti, J., Golding, H. & Sher, A. (2004) *J Biol Chem* 279, 53635-42.
53. Moore, J. P. (1993) *AIDS Res Hum Retroviruses* 9, 209-19.
54. Koito, A., Stamatatos, L. & Cheng-Mayer, C. (1995) *Virology* 206, 878-84.
55. Hoffman, N. G., Seillier-Moiseiwitsch, F., Ahn, J., Walker, J. M. & Swanstrom, R. (2002) *J Virol* 76, 3852-64.
56. Yamaguchi-Kabata, Y., Yamashita, M., Ohkura, S., Hayami, M. & Miura, T. (2004) *J Mol Evol* 58, 333-40.
57. Nabel, G. J. (2004) *AIDS Vaccine* 04 Abstract 84, 38.
58. Harrop, H. A., Coombe, D. R. & Rider, C. C. (1994) *AIDS* 8, 183-92.
59. Moulard, M., Phogat, S. K., Shu, Y., Labrijn, A. F., Xiao, X., Binley, J. M., Zhang, M. Y., Sidorov, I. A., Broder, C. C., Robinson, J., Parren, P. W., Burton, D. R. & Dimitrov, D. S. (2002) *Proc Natl Acad Sci USA* 99, 6913-8.
60. Ohshiro, Y., Murakami, T., Matsuda, K., Nishioka, K., Yoshida, K. & Yamamoto, N. (1996) *Microbiol Immunol* 40, 827-35.
61. Connier, E. G., Tran, D. N., Yukhayeva, L., Olson, W. C. & Dragic, T. (2001) *J Virol* 75, 5541-9.
62. Chabot, D. J., Zhang, P. F., Quinnan, G. V. & Broder, C. C. (1999) *J Virol* 73, 6598-609.
63. Zuker, M. & Somorjai, R. L. (1989) *Bull Math Biol* 51, 55-78.
64. May, A. C. & Johnson, M. S. (1994) *Protein Eng* 7, 475-85.
65. Diederichs, K. (1995) *Proteins* 23, 187-95.
66. Lackner, P., Koppensteiner, W. A., Sippi, M. J. & Domingues, F. S. (2000) *Protein Eng* 13, 745-52.
67. Abagyan, R. A., Totrov, M. M. & Kuznetsov, D. A. (1994) *J. Comp. Chem.* 15, 488-506.
68. Holm, L. & Sander, C. (1993) *J Mol Biol* 233, 123-38.
69. Totrov, M. & Abagyan, R. (2001) *Biopolymers* 60, 124-33.
70. Fernandez-Recio, J., Totrov, M. & Abagyan, R. (2002) *Protein Sci* 11, 280-91.
71. Needleman, S. B. & Wunsch, C. D. (1970) *J Mol Biol* 48, 443-53.
72. Abagyan, R. A. & Batalov, S. (1997) *J Mol Biol* 273, 355-68.
73. Fang, G., Burger, H., Grimson, R., Tropper, P., Nachman, S., Mayers, D., Weislow, O., Moore, R., Reyelt, C., Hutcheon, N. & et al. (1995) *Proc Natl Acad Sci USA* 92, 12100-4.
74. Fang, G., Kuiken, C., Weiser, B., Rowland-Jones, S., Plummer, F., Chen, C. H., Kaul, R., Anzala, A. O., Bwayo, J., Kimani, J., Philpott, S. M., Kitchen, C., Sinsheimer, J. S., Gaschen, B., Lang, D., Shi, B., Kemal, K. S., Rostron, T., Brunner, C., Beddows, S., Sattenau, Q., Paxinos, E., Oyugi, J. & Burger, H. (2004) *J Infect Dis* 190, 697-701.
75. Philpott, S., Weiser, B., Anastos, K., Kitchen, C. M., Robison, E., Meyer, W. A., 3rd, Sacks, H. S., Mathur-Wagh, U., Brunner, C. & Burger, H. (2001) *J Clin Invest* 107, 431-8.
76. Philpott, S., Burger, H., Tsoukas, C., Foley, B., Anastos, K., Kitchen, C. & Weiser, B. (2005) *J Virol.* 79:353-63.
77. Zhong, P., Burda, S., Konings, F., Urbanski, M., Ma, L., Zekeng, L., Ewane, L., Agyingi, L., Agwara, M., Saa, Afane, Z. E., Kinge, T., Zolla-Pazner, S. & Nyambi, P. (2003) *AIDS Res Hum Rertroviruses* 19, 1167-78.
78. Holm-Hansen, C., Stern, B., Rustad, S., Shao, J. & Asjo, B. (2000) *Apmis* 108, 608-16.

All the references cited in this document are incorporated herein by reference in their entirety, whether specifically incorporated or not.

---

What is claimed is:

1. A method for detecting, in a sample from a subject infected with or suspected of being infected with HIV-1, the presence of HIV-1 virus that is selective for X4-co- receptors (X4 virus), the method comprising:
   (i) from the amino acid sequence of at least a pan of the HIV-1 gp120 V3 region peptide that includes positions 11, 24 and 25, or
   (ii) from the nucleotide sequence of at least a part of the HIV gp120 V3 coding region comprising codons encoding the amino acids at positions 11, 24, and 25,
   identifying the amino acids at positions 11, 24 and 25, or the codons encoding said amino acids,
      wherein the finding of a positively charged amino acid, or a codon encoding a positively charged amino acid, at any one of said positions upon examination of all three positions predicts the presence of the X4 virus in the subject.

2. A method for detecting, in a sample from a subject infected with or suspected of being infected with HIV-1, the presence of HIV-virus that is selective for R5-co- receptors (R5-virus), the method comprising:
   (i) from the amino acid sequence of at least a pan of the HIV-1 gp120 V3 region peptide that includes residues 11, 24 and 25, or
   (ii) from the nucleotide sequence of at least a part of the HIV gp120 V3 coding region comprising codons encoding the amino acids at positions 11, 24, and 25,
   identifying the amino acid at position 24, or the codon encoding said amino acids,
      wherein a finding that the amino acid at position 24 is not positively charged, or that the codon does not encode an amino acid that is positively charged, predicts the presence of the R5 virus in the subject, provided that neither of the amino acids at positions 11 and 25 is positively charged or that codons encoding the amino acids at positions 11 and 25 do not encode a positively charged amino acid.

3. A method according to claim 1 wherein the amino acid of said amino acid sequence is identified.

4. A method according to claim 1 wherein the codon of said nucleotide sequence is identified.

5. A method according to claim 3 wherein, in addition to identifying said amino acid, the codon of said nucleotide sequence is identified.

6. A method according to claim 2 wherein the amino acid of said amino acid sequence is identified.

7. A method according to claim 2 wherein the codon of said nucleotide sequence is identified.

8. A method according to claim 6 wherein, in addition to identifying said amino acid, the codon of said nucleotide sequence is identified.

9. A method for determining the ratio of X4 HIV-1 virus to R5 HIV-1 virus in a subject, the method comprising:
from a sample of a body fluid, cells or tissue from a subject infected with or suspected of being infected with HIV-1, determining the ratio of
(a) sequences with a positively charged amino acid at position 24 of an amino acid sequence of at least a part of the gp120 V3 region that includes residues 11, 24 and 25, or
(b) sequences with a codon encoding said positively charged amino acid at position 24 from a nucleic acid sequence of a region that encodes said V3 region
to sequences lacking such a positively charged amino acid or said codon encoding said positively charged amino acid
thereby determining the ratio the X4 virus to the R5 virus in said subject.

10. A method according to claim 9 wherein the ratio of said amino acid sequences is determined in said sample.

11. A method according to claim 9 wherein the ratio of said codons nucleotide sequence is determined in said sample.

12. A method according to claim 10 wherein, in addition to the ratio of said amino acid sequences, the ratio of said nucleotide sequence is also determined in said sample.

13. The method of claim 1 wherein the finding of a positively charged amino acid, or a codon encoding a positively charged amino acid, at any one of positions 11, 24 or 25 of said V3 region peptide upon examination of all three positions predicts the presence of the X4 virus in the subject with 95.2% accuracy.

14. The method of claim 2 wherein the finding that the amino acid at position 24 is not positively charged, or that the codon does not encode an amino acid that is positively charged, predicts with 95.2% accuracy the presence of the R5 virus in the subject, provided that neither of the amino acids at positions 11 and 25 is positively charged or that codons encoding the amino acids at positions 11 and 25 do not encode a positively charged amino acid.

* * * * *